United States Patent
Watson et al.

(10) Patent No.: US 8,658,164 B2
(45) Date of Patent: Feb. 25, 2014

(54) METHODS AND MATERIALS FOR THE DIAGNOSIS OF PROSTATE CANCERS

(75) Inventors: James Douglas Watson, Auckland (NZ); Richard Llewellyn Sydney Forster, Pukekohe (NZ); Damian Jay White, Auckland (NZ)

(73) Assignee: Caldera Health Limited, Auckland (NZ)

( * ) Notice: Subject to any disclaimer, the term of this patent is extended or adjusted under 35 U.S.C. 154(b) by 0 days.

(21) Appl. No.: 13/539,102

(22) Filed: Jun. 29, 2012

(65) Prior Publication Data

US 2013/0115604 A1 May 9, 2013

Related U.S. Application Data

(63) Continuation-in-part of application No. 13/350,480, filed on Jan. 13, 2012, which is a continuation of application No. 13/291,980, filed on Nov. 8, 2011.

(51) Int. Cl.
*C12P 21/06* (2006.01)
*A61K 39/395* (2006.01)

(52) U.S. Cl.
USPC ............................... 424/130.1; 435/69.1

(58) Field of Classification Search
None
See application file for complete search history.

(56) References Cited

U.S. PATENT DOCUMENTS

| 4,654,301 A | 3/1987 | Anderson et al. |
| 5,516,639 A | 5/1996 | Tindall et al. |
| 5,525,473 A | 6/1996 | Hill et al. |
| 5,928,878 A | 7/1999 | Allard et al. |
| 6,632,624 B1 | 10/2003 | Degorce et al. |
| 7,094,533 B1 | 8/2006 | Lin |
| 2003/0108963 A1 | 6/2003 | Schlegel et al. |
| 2007/0224638 A1 | 9/2007 | Melanitou-McClymont |
| 2008/0057590 A1* | 3/2008 | Urdea et al. .................... 436/71 |
| 2009/0221672 A1 | 9/2009 | Zhang et al. |
| 2010/0021928 A1 | 1/2010 | Nagler et al. |
| 2010/0143247 A1 | 6/2010 | Fenske et al. |
| 2011/0306514 A1 | 12/2011 | Hewitt et al. |

FOREIGN PATENT DOCUMENTS

| WO | 2008/039774 A1 | 4/2008 |
| WO | 2008067065 A2 | 6/2008 |
| WO | 2011127219 A1 | 10/2011 |

OTHER PUBLICATIONS

Kosari et al., Cysteine-rich Secretory Protein-3: A Potential Biomarker for Prostate Cancer, Cancer Epidemiology, Biomarkers & Prevention, vol. 11, 1419-1426, Nov. 2002.*

(Continued)

*Primary Examiner* — Jim Ketter
*Assistant Examiner* — Reza Ghafoorian
(74) *Attorney, Agent, or Firm* — Janet Sleath; Speckman Law Group PLLC

(57) ABSTRACT

Methods for diagnosing the presence of prostate cancer in a subject are provided, such methods including detecting the levels of expression of multiple polypeptide biomarkers in a biological sample obtained from the subject and comparing the levels of expression with predetermined threshold levels. Levels of expression of at least two of the polypeptide markers that are above the predetermined threshold levels are indicative of the presence of prostate cancer in the subject. Determination of the expression levels of specific combinations of biomarkers can also be used to determine the type and/or stage of prostate cancer.

5 Claims, 10 Drawing Sheets

(56) References Cited

OTHER PUBLICATIONS

Dorff et al., Clinical and Correlative Results of SWOG S0354: A Phase II Trial of CNTO328 (Siltuximab), a Monoclonal Antibody against Interleukin-6, in Chemotherapy-Pretreated Patients with Castration-Resistant Prostate Cancer, Clin Cancer Res; 16(11) Jun. 1, 2010.*

Cooper et al., Bone Alkaline Phosphatase and Prostate-Specific Antigen in the Monitoring of Prostate Cancer, The Prostate 25:236-242 (I 994).*

Calvo et al., Alterations in Gene Expression Profiles during Prostate Cancer Progression: Functional Correlations to Tumorigenicity and Down-Regulation of Selenoprotein-P in Mouse and Human Tumors, Cancer Research 62, 5325-5335, Sep. 15, 2002.*

Hood, Brian L. et al., "Proteomic Analysis of Formalin-fixed Prostate Cancer Tissue," Molecular & Cellular Proteomics, vol. 4, pp. 1741-1753 (2005).

Ling, Michael M. et al., "Multiplexing molecular diagnostics and immunoassays using emerging microarray technologies," Expert Rev. Mol. Diagn, vol. 7, No. 1, pp. 87-98 (2007).

Madu, Chikezie O. et al., "Novel diagnostic biomarkers for prostate cancer," Journal of Cancer, vol. 1, pp. 150-177 (Oct. 6, 2010).

Sardana, Girish et al., "Emerging Biomarkers for the Diagnosis and Prognosis of Prostate Cancer," Clinical Chemistry, vol. 54, No. 12, pp. 1951-1960 (2008).

Beer, Thomas M. et al., "Double-Blinded Randomized Study of High-Dose Calcitriol Plus Docetaxel Compared With Placebo Plus Docetaxel in Androgen-Independent Prostate Cancer: A Report From the ASCENT Investigators," Journal of Clinical Oncology, vol. 25, No. 6, pp. 669-674 (2007).

Berruti, A et al., "Independent prognostic role of circulating chromogranin A in prostate cancer patients with hormone-refractory disease," Endocrine-Related Cancer, vol. 12, pp. 109-117 (2005).

Castelli, Tommaso et al., "Molecular markers for prostate cancer," Frontiers in Bioscience, Elite Edition, vol. 2, pp. 641-656 (Jan. 1, 2010).

Lorente, J.A. et al., "Clinical Efficacy of Bone Alkaline Phosphatase and Prostate Specific Antigen in the Diagnosis of Bone Metastasis in Prostate Cancer," The Journal of Urology, vol. 155, pp. 1348-1351 (Apr. 1996).

Ramirez, M.L. et al., "Beyond Prostate-Specific Antigen: Alternate Serum Markers," Prostate Cancer Prostatic Dis., vol. 11, No. 3, pp. 216-229 (2008).

Xu, Welhong et al., "Human transcription array for high-throughput clinical studies," Proc. Natl. Acad. Sci. USA, vol. 108, No. 9, pp. 3207-3712 (Mar. 1, 2011).

* cited by examiner

FIGURE 2G

SEQUENCE LISTING

<160> NUMBER OF SEQ ID NOS: 14

<210> SEQ ID NO 1
<211> LENGTH: 261

<212> TYPE: PRT
<213> ORGANISM: Homo sapiens

<400> SEQUENCE: 1

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 2
<211> LENGTH: 69
<212> TYPE: PRT
<213> ORGANISM: Homo sapiens

<400> SEQUENCE: 2

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Lys
65

```
<210> SEQ ID NO 3
<211> LENGTH: 218
<212> TYPE: PRT
<213> ORGANISM: Homo sapiens

<400> SEQUENCE: 3

Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Lys Pro Gly Asp Ser Ser His Asp Leu Met Leu
 65                  70                  75                  80

Leu Arg Leu Ser Glu Pro Ala Glu Leu Thr Asp Ala Val Lys Val Met
                 85                  90                  95

Asp Leu Pro Thr Gln Glu Pro Ala Leu Gly Thr Thr Cys Tyr Ala Ser
                100                 105                 110

Gly Trp Gly Ser Ile Glu Pro Glu Glu Phe Leu Thr Pro Lys Lys Leu
            115                 120                 125

Gln Cys Val Asp Leu His Val Ile Ser Asn Asp Val Cys Ala Gln Val
130                 135                 140

His Pro Gln Lys Val Thr Lys Phe Met Leu Cys Ala Gly Arg Trp Thr
145                 150                 155                 160

Gly Gly Lys Ser Thr Cys Ser Gly Asp Ser Gly Gly Pro Leu Val Cys
                165                 170                 175

Asn Gly Val Leu Gln Gly Ile Thr Ser Trp Gly Ser Glu Pro Cys Ala
            180                 185                 190

Leu Pro Glu Arg Pro Ser Leu Tyr Thr Lys Val Val His Tyr Arg Lys
        195                 200                 205

Trp Ile Lys Asp Thr Ile Val Ala Asn Pro
    210                 215

<210> SEQ ID NO 4
<211> LENGTH: 238
<212> TYPE: PRT
<213> ORGANISM: Homo sapiens

<400> SEQUENCE: 4

Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Leu Arg Leu Ser Glu
            115                 120                 125
```

Pro Ala Glu Leu Thr Asp Ala Val Lys Val Met Asp Leu Pro Thr Gln
            130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                    165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
                195                 200                 205

Cys Ser Trp Val Ile Leu Ile Thr Glu Leu Thr Met Pro Ala Leu Pro
210                 215                 220

Met Val Leu His Gly Ser Leu Val Pro Trp Arg Gly Val
225                 230                 235

<210> SEQ ID NO 5
<211> LENGTH: 261
<212> TYPE: PRT
<213> ORGANISM: Homo sapiens

<400> SEQUENCE: 5

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
                20                  25                  30

Lys His Ser Gln Pro Trp Gln Val Ala Val Tyr Ser His Gly Trp Ala
            35                  40                  45

His Cys Gly Gly Val Leu Val His Pro Gln Trp Val Leu Thr Ala Ala
        50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro
            260

<210> SEQ ID NO 6
<211> LENGTH: 223
<212> TYPE: PRT
<213> ORGANISM: Homo sapiens

<400> SEQUENCE: 6

Met Trp Asp Leu Val Leu Ser Ile Ala Leu Ser Val Gly Cys Thr Gly
1               5                   10                  15

Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Val Ser His Pro Tyr Ser Gln His Leu Glu Gly Lys Gly
    210                 215                 220

<210> SEQ ID NO 7
<211> LENGTH: 457
<212> TYPE: PRT
<213> ORGANISM: Homo sapiens

<400> SEQUENCE: 7

Met Arg Ser Ala Ala Val Leu Ala Leu Leu Leu Cys Ala Gly Gln Val
1               5                   10                  15

Thr Ala Leu Pro Val Asn Ser Pro Met Asn Lys Gly Asp Thr Glu Val
            20                  25                  30

Met Lys Cys Ile Val Glu Val Ile Ser Asp Thr Leu Ser Lys Pro Ser
        35                  40                  45

Pro Met Pro Val Ser Gln Glu Cys Phe Glu Thr Leu Arg Gly Asp Glu
    50                  55                  60

Arg Ile Leu Ser Ile Leu Arg His Gln Asn Leu Leu Lys Glu Leu Gln
65                  70                  75                  80

Asp Leu Ala Leu Gln Gly Ala Lys Glu Arg Ala His Gln Gln Lys Lys
                85                  90                  95

His Ser Gly Phe Glu Asp Glu Leu Ser Glu Val Leu Glu Asn Gln Ser
            100                 105                 110

Ser Gln Ala Glu Leu Lys Glu Ala Val Glu Pro Ser Lys Asp
        115                 120                 125

Val Met Glu Lys Arg Glu Asp Ser Lys Glu Ala Glu Lys Ser Gly Glu
130                 135                 140

Ala Thr Asp Gly Ala Arg Pro Gln Ala Leu Pro Glu Pro Met Gln Glu
145                 150                 155                 160

Ser Lys Ala Glu Gly Asn Asn Gln Ala Pro Gly Glu Glu Glu Glu
            165                 170                 175

Glu Glu Glu Ala Thr Asn Thr His Pro Pro Ala Ser Leu Pro Ser Gln
            180                 185                 190

Lys Tyr Pro Gly Pro Gln Ala Glu Gly Asp Ser Glu Gly Leu Ser Gln
        195                 200                 205

Gly Leu Val Asp Arg Glu Lys Gly Leu Ser Ala Glu Pro Gly Trp Gln
210                 215                 220

Ala Lys Arg Glu Glu Glu Glu Glu Glu Glu Ala Glu Ala Gly
225                 230                 235                 240

Glu Glu Ala Val Pro Glu Glu Gly Pro Thr Val Val Leu Asn Pro
            245                 250                 255

His Pro Ser Leu Gly Tyr Lys Glu Ile Arg Lys Gly Glu Ser Arg Ser
        260                 265                 270

Glu Ala Leu Ala Val Asp Gly Ala Gly Lys Pro Gly Ala Glu Glu Ala
        275                 280                 285

Gln Asp Pro Glu Gly Lys Gly Glu Gln Glu His Ser Gln Gln Lys Glu
        290                 295                 300

Glu Glu Glu Glu Met Ala Val Val Pro Gln Gly Leu Phe Arg Gly Gly
305                 310                 315                 320

Lys Ser Gly Glu Leu Glu Gln Glu Glu Glu Arg Leu Ser Lys Glu Trp
            325                 330                 335

Glu Asp Ser Lys Arg Trp Ser Lys Met Asp Gln Leu Ala Lys Glu Leu
            340                 345                 350

Thr Ala Glu Lys Arg Leu Glu Gly Gln Glu Glu Glu Asp Asn Arg
        355                 360                 365

Asp Ser Ser Met Lys Leu Ser Phe Arg Ala Arg Ala Tyr Gly Phe Arg
370                 375                 380

Gly Pro Gly Pro Gln Leu Arg Arg Gly Trp Arg Pro Ser Ser Trp Glu
385                 390                 395                 400

Asp Ser Leu Glu Ala Gly Leu Pro Leu Gln Val Arg Gly Tyr Pro Glu
            405                 410                 415

Glu Lys Lys Glu Glu Gly Ser Ala Asn Arg Arg Pro Glu Asp Gln
            420                 425                 430

Glu Leu Glu Ser Leu Ser Ala Ile Glu Ala Glu Leu Glu Lys Val Ala
        435                 440                 445

His Gln Leu Gln Ala Leu Arg Arg Gly
    450                 455

<210> SEQ ID NO 8
<211> LENGTH: 224
<212> TYPE: PRT
<213> ORGANISM: Homo sapiens

<400> SEQUENCE: 8

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

```
Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
 50                  55                  60

Arg Gly Thr Val Phe Ser Arg Met Pro Pro Arg Asp Lys Thr Met Arg
 65                  70                  75                  80

Phe Phe Ile Phe Trp Ser Lys Asp Ile Gly Tyr Ser Phe Thr Val Gly
                 85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
210                 215                 220

<210> SEQ ID NO 9
<211> LENGTH: 386
<212> TYPE: PRT
<213> ORGANISM: Homo sapiens

<400> SEQUENCE: 9

Met Arg Ala Ala Pro Leu Leu Leu Ala Arg Ala Ala Ser Leu Ser Leu
 1               5                  10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
 50                  55                  60

Gln Gly Phe Gly Gln Leu Thr Gln Leu Gly Met Glu Gln His Tyr Glu
 65                  70                  75                  80

Leu Gly Glu Tyr Ile Arg Lys Arg Tyr Arg Lys Phe Leu Asn Glu Ser
                 85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190
```

```
Lys Leu Ser Gly Leu His Gly Gln Asp Leu Phe Gly Ile Trp Ser Lys
            195                 200                 205

Val Tyr Asp Pro Leu Tyr Cys Glu Ser Val His Asn Phe Thr Leu Pro
        210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
370                 375                 380

Thr Asp
385

<210> SEQ ID NO 10
<211> LENGTH: 332
<212> TYPE: PRT
<213> ORGANISM: Homo sapiens

<400> SEQUENCE: 10

Met Ala Thr Ile Lys Ser Glu Leu Ile Lys Asn Phe Ala Glu Glu Glu
1               5                   10                  15

Ala Ile His His Asn Lys Ile Ser Ile Val Gly Thr Gly Ser Val Gly
            20                  25                  30

Val Ala Cys Ala Ile Ser Ile Leu Leu Lys Gly Leu Ser Asp Glu Leu
        35                  40                  45

Val Leu Val Asp Val Asp Glu Gly Lys Leu Lys Gly Glu Thr Met Asp
    50                  55                  60

Leu Gln His Gly Ser Pro Phe Met Lys Met Pro Asn Ile Val Ser Ser
65                  70                  75                  80

Lys Asp Tyr Leu Val Thr Ala Asn Ser Asn Leu Val Ile Ile Thr Ala
                85                  90                  95

Gly Ala Arg Gln Lys Lys Gly Glu Thr Arg Leu Asp Leu Val Gln Arg
            100                 105                 110

Asn Val Ser Ile Phe Lys Leu Met Ile Pro Asn Ile Thr Gln Tyr Ser
        115                 120                 125

Pro His Cys Lys Leu Leu Ile Val Thr Asn Pro Val Asp Ile Leu Thr
    130                 135                 140

Tyr Val Ala Trp Lys Leu Ser Gly Phe Pro Lys Asn Arg Val Ile Gly
145                 150                 155                 160

Ser Gly Cys Asn Leu Asp Ser Ala Arg Phe Arg Tyr Phe Ile Gly Gln
                165                 170                 175
```

```
Arg Leu Gly Ile His Ser Glu Ser Cys His Gly Leu Ile Leu Gly Glu
            180                 185                 190

His Gly Asp Ser Ser Val Pro Val Trp Ser Gly Val Asn Ile Ala Gly
            195                 200                 205

Val Pro Leu Lys Asp Leu Asn Pro Asp Ile Gly Thr Asp Lys Asp Pro
210                 215                 220

Glu Gln Trp Glu Asn Val His Lys Lys Val Ile Ser Ser Gly Tyr Glu
225                 230                 235                 240

Met Val Lys Met Lys Gly Tyr Thr Ser Trp Gly Ile Ser Leu Ser Val
                245                 250                 255

Ala Asp Leu Thr Glu Ser Ile Leu Lys Asn Leu Arg Arg Val His Pro
            260                 265                 270

Val Ser Thr Leu Ser Lys Gly Leu Tyr Gly Ile Asn Glu Asp Ile Phe
            275                 280                 285

Leu Ser Val Pro Cys Ile Leu Gly Glu Asn Gly Ile Thr Asp Leu Ile
            290                 295                 300

Lys Val Lys Leu Thr Leu Glu Glu Glu Ala Cys Leu Gln Lys Ser Ala
305                 310                 315                 320

Glu Thr Leu Trp Glu Ile Gln Lys Glu Leu Lys Leu
                325                 330

<210> SEQ ID NO 11
<211> LENGTH: 334
<212> TYPE: PRT
<213> ORGANISM: Homo sapiens

<400> SEQUENCE: 11

Met Ala Thr Leu Lys Glu Lys Leu Ile Ala Pro Val Ala Glu Glu Glu
1               5                   10                  15

Ala Thr Val Pro Asn Asn Lys Ile Thr Val Val Gly Val Gly Gln Val
                20                  25                  30

Gly Met Ala Cys Ala Ile Ser Ile Leu Gly Lys Ser Leu Ala Asp Glu
            35                  40                  45

Leu Ala Leu Val Asp Val Leu Glu Asp Lys Leu Lys Gly Glu Met Met
        50                  55                  60

Asp Leu Gln His Gly Ser Leu Phe Leu Gln Thr Pro Lys Ile Val Ala
65                  70                  75                  80

Asp Lys Asp Tyr Ser Val Thr Ala Asn Ser Lys Ile Val Val Val Thr
                85                  90                  95

Ala Gly Val Arg Gln Gln Glu Gly Glu Ser Arg Leu Asn Leu Val Gln
            100                 105                 110

Arg Asn Val Asn Val Phe Lys Phe Ile Ile Pro Gln Ile Val Lys Tyr
        115                 120                 125

Ser Pro Asp Cys Ile Ile Ile Val Val Ser Asn Pro Val Asp Ile Leu
130                 135                 140

Thr Tyr Val Thr Trp Lys Leu Ser Gly Leu Pro Lys His Arg Val Ile
145                 150                 155                 160

Gly Ser Gly Cys Asn Leu Asp Ser Ala Arg Phe Arg Tyr Leu Met Ala
                165                 170                 175

Glu Lys Leu Gly Ile His Pro Ser Ser Cys His Gly Trp Ile Leu Gly
            180                 185                 190

Glu His Gly Asp Ser Ser Val Ala Val Trp Ser Gly Val Asn Val Ala
        195                 200                 205

Gly Val Ser Leu Gln Glu Leu Asn Pro Glu Met Gly Thr Asp Asn Asp
210                 215                 220
```

```
Ser Glu Asn Trp Lys Glu Val His Lys Met Val Val Glu Ser Ala Tyr
225                 230                 235                 240

Glu Val Ile Lys Leu Lys Gly Tyr Thr Asn Trp Ala Ile Gly Leu Ser
            245                 250                 255

Val Ala Asp Leu Ile Glu Ser Met Leu Lys Asn Leu Ser Arg Ile His
        260                 265                 270

Pro Val Ser Thr Met Val Lys Gly Met Tyr Gly Ile Glu Asn Glu Val
    275                 280                 285

Phe Leu Ser Leu Pro Cys Ile Leu Asn Ala Arg Gly Leu Thr Ser Val
290                 295                 300

Ile Asn Gln Lys Leu Lys Asp Asp Glu Val Ala Gln Leu Lys Lys Ser
305                 310                 315                 320

Ala Asp Thr Leu Trp Asp Ile Gln Lys Asp Leu Lys Asp Leu
            325                 330

<210> SEQ ID NO 12
<211> LENGTH: 332
<212> TYPE: PRT
<213> ORGANISM: Homo sapiens

<400> SEQUENCE: 12

Met Ser Thr Val Lys Glu Gln Leu Ile Glu Lys Leu Ile Glu Asp Asp
1               5                   10                  15

Glu Asn Ser Gln Cys Lys Ile Thr Ile Val Gly Thr Gly Ala Val Gly
            20                  25                  30

Met Ala Cys Ala Ile Ser Ile Leu Leu Lys Asp Leu Ala Asp Glu Leu
        35                  40                  45

Ala Leu Val Asp Val Ala Leu Asp Lys Leu Lys Gly Glu Met Met Asp
    50                  55                  60

Leu Gln His Gly Ser Leu Phe Phe Ser Thr Ser Lys Ile Thr Ser Gly
65                  70                  75                  80

Lys Asp Tyr Ser Val Ser Ala Asn Ser Arg Ile Val Ile Val Thr Ala
                85                  90                  95

Gly Ala Arg Gln Gln Glu Gly Glu Thr Arg Leu Ala Leu Val Gln Arg
            100                 105                 110

Asn Val Ala Ile Met Lys Ser Ile Ile Pro Ala Ile Val His Tyr Ser
        115                 120                 125

Pro Asp Cys Lys Ile Leu Val Val Ser Asn Pro Val Asp Ile Leu Thr
    130                 135                 140

Tyr Ile Val Trp Lys Ile Ser Gly Leu Pro Val Thr Arg Val Ile Gly
145                 150                 155                 160

Ser Gly Cys Asn Leu Asp Ser Ala Arg Phe Arg Tyr Leu Ile Gly Glu
                165                 170                 175

Lys Leu Gly Val His Pro Thr Ser Cys His Gly Trp Ile Ile Gly Glu
            180                 185                 190

His Gly Asp Ser Ser Val Pro Leu Trp Ser Gly Val Asn Val Ala Gly
        195                 200                 205

Val Ala Leu Lys Thr Leu Asp Pro Lys Leu Gly Thr Asp Ser Asp Lys
    210                 215                 220

Glu His Trp Lys Asn Ile His Lys Gln Val Ile Gln Ser Ala Tyr Glu
225                 230                 235                 240

Ile Ile Lys Leu Lys Gly Tyr Thr Ser Trp Ala Ile Gly Leu Ser Val
                245                 250                 255

Met Asp Leu Val Gly Ser Ile Leu Lys Asn Leu Arg Arg Val His Pro
            260                 265                 270
```

```
Val Ser Thr Met Val Lys Gly Leu Tyr Gly Ile Lys Glu Glu Leu Phe
        275                 280                 285
Leu Ser Ile Pro Cys Val Leu Gly Arg Asn Gly Val Ser Asp Val Val
        290                 295                 300
Lys Ile Asn Leu Asn Ser Glu Glu Glu Ala Leu Phe Lys Lys Ser Ala
305                 310                 315                 320
Glu Thr Leu Trp Asn Ile Gln Lys Asp Leu Ile Phe
                325                 330

<210> SEQ ID NO 13
<211> LENGTH: 524
<212> TYPE: PRT
<213> ORGANISM: Homo sapiens

<400> SEQUENCE: 13

Met Ile Ser Pro Phe Leu Val Leu Ala Ile Gly Thr Cys Leu Thr Asn
1               5                   10                  15
Ser Leu Val Pro Glu Lys Glu Lys Asp Pro Lys Tyr Trp Arg Asp Gln
            20                  25                  30
Ala Gln Glu Thr Leu Lys Tyr Ala Leu Glu Leu Gln Lys Leu Asn Thr
        35                  40                  45
Asn Val Ala Lys Asn Val Ile Met Phe Leu Gly Asp Gly Met Gly Val
    50                  55                  60
Ser Thr Val Thr Ala Ala Arg Ile Leu Lys Gly Gln Leu His His Asn
65                  70                  75                  80
Pro Gly Glu Glu Thr Arg Leu Glu Met Asp Lys Phe Pro Phe Val Ala
                85                  90                  95
Leu Ser Lys Thr Tyr Asn Thr Asn Ala Gln Val Pro Asp Ser Ala Gly
            100                 105                 110
Thr Ala Thr Ala Tyr Leu Cys Gly Val Lys Ala Asn Glu Gly Thr Val
        115                 120                 125
Gly Val Ser Ala Ala Thr Glu Arg Ser Arg Cys Asn Thr Thr Gln Gly
    130                 135                 140
Asn Glu Val Thr Ser Ile Leu Arg Trp Ala Lys Asp Ala Gly Lys Ser
145                 150                 155                 160
Val Gly Ile Val Thr Thr Thr Arg Val Asn His Ala Thr Pro Ser Ala
                165                 170                 175
Ala Tyr Ala His Ser Ala Asp Arg Asp Trp Tyr Ser Asp Asn Glu Met
            180                 185                 190
Pro Pro Glu Ala Leu Ser Gln Gly Cys Lys Asp Ile Ala Tyr Gln Leu
        195                 200                 205
Met His Asn Ile Arg Asp Ile Asp Val Ile Met Gly Gly Gly Arg Lys
    210                 215                 220
Tyr Met Tyr Pro Lys Asn Lys Thr Asp Val Glu Tyr Glu Ser Asp Glu
225                 230                 235                 240
Lys Ala Arg Gly Thr Arg Leu Asp Gly Leu Asp Leu Val Asp Thr Trp
                245                 250                 255
Lys Ser Phe Lys Pro Arg Tyr Lys His Ser His Phe Ile Trp Asn Arg
            260                 265                 270
Thr Glu Leu Leu Thr Leu Asp Pro His Asn Val Asp Tyr Leu Leu Gly
        275                 280                 285
Leu Phe Glu Pro Gly Asp Met Gln Tyr Glu Leu Asn Arg Asn Asn Val
    290                 295                 300
Thr Asp Pro Ser Leu Ser Glu Met Val Val Val Ala Ile Gln Ile Leu
305                 310                 315                 320
```

Arg Lys Asn Pro Lys Gly Phe Phe Leu Leu Val Glu Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
    450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
    515                 520

<210> SEQ ID NO 14
<211> LENGTH: 268
<212> TYPE: PRT
<213> ORGANISM: Homo sapiens

<400> SEQUENCE: 14

Met Lys Gln Ile Leu His Pro Ala Leu Glu Thr Thr Asp Pro Cys Ser
1               5                   10                  15

Thr Gly Phe Val Phe Pro Ala Met Thr Leu Phe Pro Val Leu Leu Phe
                20                  25                  30

Leu Val Ala Gly Leu Leu Pro Ser Phe Pro Ala Asn Glu Asp Lys Asp
            35                  40                  45

Pro Ala Phe Tyr Ala Leu Leu Thr Thr Gln Thr Gln Val Gln Arg Glu
        50                  55                  60

Ile Val Asn Lys His Asn Glu Leu Arg Arg Ala Val Ser Pro Pro Ala
65                  70                  75                  80

Arg Asn Met Leu Lys Met Glu Trp Asn Lys Glu Ala Ala Ala Asn Ala
                85                  90                  95

Gln Lys Trp Ala Asn Gln Cys Asn Tyr Arg His Ser Asn Pro Lys Asp
            100                 105                 110

Arg Met Thr Ser Leu Lys Cys Gly Glu Asn Leu Tyr Met Ser Ser Ala
        115                 120                 125

Ser Ser Ser Trp Ser Gln Ala Ile Gln Ser Trp Phe Asp Glu Tyr Asn
    130                 135                 140

Asp Phe Asp Phe Gly Val Gly Pro Lys Thr Pro Asn Ala Val Val Gly
145                 150                 155                 160

His Tyr Thr Gln Val Val Trp Tyr Ser Ser Tyr Leu Val Gly Cys Gly
                165                 170                 175

-continued

```
Asn Ala Tyr Cys Pro Asn Gln Lys Val Leu Lys Tyr Tyr Tyr Val Cys
            180             185             190

Gln Tyr Cys Pro Ala Gly Asn Trp Ala Asn Arg Leu Tyr Val Pro Tyr
        195             200             205

Glu Gln Gly Ala Pro Cys Ala Ser Cys Pro Asp Asn Cys Asp Asp Gly
    210             215             220

Leu Cys Thr Asn Gly Cys Lys Tyr Glu Asp Leu Tyr Ser Asn Cys Lys
225             230             235             240

Ser Leu Lys Leu Thr Leu Thr Cys Lys His Gln Leu Val Arg Asp Ser
            245             250             255

Cys Lys Ala Ser Cys Asn Cys Ser Asn Ser Ile Tyr
            260             265
```

METHODS AND MATERIALS FOR THE DIAGNOSIS OF PROSTATE CANCERS

REFERENCE TO RELATED APPLICATIONS

This application is a continuation-in-part of U.S. patent application Ser. No. 13/350,480, filed Jan. 13, 2012, which is a continuation of U.S. patent application Ser. No. 13/291,980, filed Nov. 8, 2011, the disclosures of which are hereby incorporated by reference.

REFERENCE TO SEQUENCE LISTING

This application incorporates by reference in its entirety the Sequence Listing contained in the accompanying file, named "1003CIP_seqlist.txt," the size of which is 32 KB, and which was created on Jun. 27, 2012.

TECHNICAL FIELD

The present disclosure relates to methods and compositions for diagnosing, and monitoring the progress of, prostate cancer.

BACKGROUND

The use of prostate specific antigen (PSA) as a diagnostic biomarker for prostate cancer was approved by the US Federal Drug Agency in 1994. In the nearly two decades since this approval, the PSA test has remained the primary tool for use in prostate cancer diagnosis, in monitoring for recurrence of prostate cancer, and in following the efficacy of treatments. However the PSA test has multiple shortcomings and, despite its widespread use, has resulted in only small changes in the death rate from advanced prostate cancers. To reduce the death rate and the negative impacts on quality of life caused by prostate cancer, new tools are required not only for more accurate primary diagnosis, but also for assessing the risk of spread of primary prostate cancers, and for monitoring responses to therapeutic interventions.

Today, a blood serum level of around 4 ng per ml of PSA is considered indicative of prostate cancer, while a PSA level of 10 ng per ml or higher is considered highly suggestive of prostate cancer.

The PSA blood test is not used in isolation when checking for prostate cancer; a digital rectal examination (DRE) is usually also performed. If the results of the PSA test or the DRE are abnormal, a biopsy is generally performed in which small samples of tissue are removed from the prostate and examined. If the results are positive for prostate cancer, further tests may be needed to determine the stage of progression of the cancer, such as a bone scan, a computed tomography (CT) scan or a pelvic lymph node dissection.

While the PSA test has a good sensitivity (80%), it suffers from a false positive rate that approaches 75%. For example, it has been estimated that for PSA values of 4-10 ng/ml, only one true diagnosis of prostate cancer was found in approximately four biopsies performed (Catalona et al. (1994) J. Urol. 151(5): 1283-90). Tests that measure the ratio of free to total (i.e., free plus bound) PSA do not have significantly greater specificity or sensitivity than the standard PSA test.

Higher PSA levels often lead to biopsies to determine the presence or absence of cancer cells in the prostate, and may lead to the surgical removal of the localized prostate gland. While surgery removes the localized cancer and often improves prostate cancer-specific mortality, it also masks the fact that many patients with prostate cancer, even in the absence of surgery, do not experience disease progression to metastasis or death.

Currently, the established prognostic factors of histological grade and cancer stage from biopsy results, and prostate-specific antigen level in blood at diagnosis are insufficient to separate prostate cancer patients who are at high risk for cancer progression from those who are likely to die of another cause.

Once virulent forms of prostate cancer have been diagnosed, control strategies may involve surgery to remove the prostate gland if identified before metastasis, radiation to destroy cancer cells within the prostate, and drug-based testosterone repression, generally referred to as androgen depletion therapy. These various treatments may bring about cures in some instances, or slow the time to death. However, for those with the most virulent forms of prostate cancer, the cancer will usually recur after surgery or radiation therapy and progress to resistance to androgen depletion therapy, with death a frequent outcome.

Early detection of virulent forms of prostate cancer is critical but the conclusion of specialist physicians is that the PSA test alone is inadequate for distinguishing patients whose cancers will become virulent and progress to threaten life expectancy from those with indolent cancers.

The following are some key reasons why the PSA test does not meet the needs of men's health:

i) The Type of Cancer

There are at least two basic cell types involved in prostate cancer. Adenocarcinoma is a cancer of epithelial cells in the prostate gland and accounts for approximately 95% of prostate cancers. Neuroendocrine cancers may arise from cells of the endocrine (hormonal) and nervous systems of the prostate gland and account for approximately 5% of prostate cancers. Neuroendocrine cells have common features such as special secretory granules, produce biogenic amines and polypeptide hormones, and are most common in the intestine, lung, salivary gland, pituitary gland, pancreas, liver, breast and prostate. Neuroendocrine cells co-proliferate with malignant adenocarcinomas and secrete factors which appear to stimulate adenocarcinoma cell growth. Neuroendocrine cancers are rarer, and are considered non-PSA secreting and androgen-independent for their growth.

ii) Asymptomatic Men

Some 15 to 17% of men with prostate cancer have cancers that grow but do not produce increasing or high blood levels of PSA. In these patients, who are termed asymptomatic, the PSA test often returns false negative test results as the cancer grows.

iii) BPH, Prostatitis and PIN

Benign prostate hypertrophy (BPH), a non-malignant growth of epithelial cells, and prostatitis are diseases of the prostate that are usually caused by an infection of the prostate gland. Both BPH and prostatitis are common in men over 50 and can result in increased PSA levels. Incidence rates increase from 3 cases per 1000 man-years at age 45-49 years, to 38 cases per 1000 man-years by the age of 75-79 years. Whereas the prevalence rate is 2.7% for men aged 45-49, it increases to at least 24% by the age of 80 years. While prostate cancer results from the deregulated proliferation of epithelial cells, BPH commonly results from proliferation of normal epithelial cells and frequently does not lead to malignancy (Ziada et al. (1999) Urology 53(3 Suppl 3D): 1-6). Prostatitis in males is frequently attributed to an infection in prostate tissue including infection by *E. coli, Klebsiella* sp., *Serratia* and/or *Pseudomonas* sp.

Another condition, known as prostate intraepithelial neoplasia (PIN), may precede prostate cancer by five to ten years. Currently there are no specific diagnostic tests for PIN, although the ability to detect and monitor this potentially pre-cancerous condition would contribute to early detection and enhanced survival rates for prostate cancer.

iv) The Phenotype of the Prostate Cancer

The phenotype of prostate cancer varies from one patient to another. More specifically, in different individuals prostate cancers display heterogeneous cellular morphologies, growth rates, responsiveness to androgens and pharmacological blocking agents for androgens, and varying metastatic potential. Each prostate cancer has its own unique progression involving multiple steps, including progression from localized carcinoma to invasive carcinoma to metastasis. The progression of prostate cancer likely proceeds, as seen for other cancers, via events that include the loss of function of cell regulators such as cancer suppressors, cell cycle and apoptosis regulators, proteins involved in metabolism and stress response, and metastasis related molecules (Abate-Shen et al. (2000) Polypeptides Dev. 14(19):2410-34; Ciocca et al. (2005) Cell Stress Chaperones 10(2):86-103).

There is unlikely to be one diagnostic test that detects all forms of primary prostate cancer, or one prognostic test for all routes to metastasis. Further tests are therefore needed before prostate cancer can be diagnosed in its different forms.

At present health authorities, do not universally recommend widespread screening for prostate cancer with the PSA test. There are concerns that many men may be diagnosed and treated unnecessarily as a result of being screened, at high cost to health systems as well as risking the patient's quality of life, such as through incontinence or impotence. Despite these concerns, prostate cancer is the most prevalent form of cancer and the second most common cause of cancer death in New Zealand, Australian and North American males (Jemal et al. (2007) CA Cancer J. Clin. 57(1):43-66). In reality, at least some of the men incubating life threatening forms of prostate cancer are being missed until their cancer is too advanced, due to the economic costs of national screening, the need to avoid unnecessary over-treatment, and/or the presence of progressive cancers producing only low or background levels of PSA. The need for a better diagnostic test could not be clearer.

An important clinical question is how aggressively to treat patients with localized prostate cancer. Treatment options for more aggressive cancers are invasive and include radical prostatectomy and/or radiation therapy. Androgen-depletion therapy, for example using gonadotropin-releasing hormone agonists (e.g., leuprolide, goserelin, etc.), is designed to reduce the amount of testosterone that enters the prostate gland and is used in patients with metastatic disease, some patients who have a rising PSA and choose not to have surgery or radiation, and some patients with a rising PSA after surgery or radiation. Treatment options usually depend on the stage of the prostate cancer. Men with a 10-year life expectancy or less, who have a low Gleason score from a biopsy and whose cancer has not spread beyond the prostate are often not treated. Younger men with a low Gleason score and a prostate-restricted cancer may enter a phase of "watchful waiting" in which treatment is withheld until signs of progression are identified. However, these prognostic indicators do not accurately predict clinical outcome for individual patients.

Unlike many cancer types, specific patterns of oncogene expression have not been consistently identified in prostate cancer progression, although a number of candidate genes and pathways likely to be important in individual cases have been identified (Tomlins et al., Annu. Rev. Pathol. 1:243-71, 2006). Several groups have attempted to examine prostate cancer progression by comparing gene expression of primary carcinomas to normal prostate. Because of differences in technique, as well as the true biologic heterogeneity seen in prostate cancer, these studies have reported thousands of candidate genes but shared only moderate consensus.

A few genes have emerged including hepsin (HPN; Rhodes et al., Cancer Res. 62:4427-33, 2002), alpha-methylacyl-CoA racemase (AMACR; Rubin et al., JAMA 287:1662-70, 2002) and enhancer of Zeste homolog 2 (EZH2; Varambally et al., Nature 419:624-9, 2002), which have been shown experimentally to have probable roles in prostate carcinogenesis. Most recently, bioinformatic approaches and gene expression methods have been used to identify fusion of androgen-regulated genes including transmembrane protease, serine 2 (TMPRSS2) with members of the erythroblast transformation specific (ETS) DNA transcription factor family (Tomlins et al., Science 310:644-8, 2005). These fusions appear commonly in prostate cancers and have been shown to be prevalent in more aggressive cancers (Attard et al., Oncogene 27:253-63, 2008; Demichelis et al., Oncogene 26:4596-9, 2007; Nam et al., Br. J. Cancer 97:1690-5, 2007). A number of studies have shown distinct classes of cancers separable by their gene expression profiles (Rhodes et al., Cancer Res. 62:4427-33, 2002; Glinsky et al., J. Clin. Invest. 113:913-23, 2004; Lapointe et al., Proc. Natl. Acad. Sci. USA 101:811-6, 2004; Singh et al., Cancer Cell 1:203-9, 2002; Yu et al., J. Clin. Oncol. 22:2790-9, 2004). In addition, a number of gene expression studies have been performed looking for gene dysregulation in metastatic prostate cancers when compared to normal (healthy) prostate tissue (Varambally et al., Nature 419:624-9, 2002; Lapointe et al., Proc. Natl. Acad. Sci. USA 101:811-6, 2004; LaTulippe et al., Cancer Res. 62:4499-506, 2002). One factor impacting clinical utility of gene expression analyses is the fact that most samples available for validation exist only as formalin fixed paraffin embedded (FFPE) tissues. In contrast, many of the cDNA microarray studies have used snap frozen tissues (Bibikova et al., Genomics 89:666-72, 2007; van't Veer et al., Nature 415:530-6, 2002).

There are a range of blood proteins whose levels change in subjects as prostate cancer develops. Some of these are produced by prostate cancer cells themselves, while others are produced by cells of non-prostate origin.

PSA is a class of protein that is produced by both healthy and cancerous prostate tissues. Another class of proteins that change as prostate cancer develops are immune system products. These can be divided into immune specific products, such as antibodies, and immune nonspecific products, such as growth factors and acute phase proteins.

Acute-phase proteins are a class of proteins whose plasma concentrations increase in response to inflammation. In response to injury and cancer cell growth, local inflammatory cells (neutrophils, granulocytes and macrophages) secrete a number of cytokines into the bloodstream, most notable of which are the interleukins IL-1, IL-6 and IL-8, and TNF-α. As a result, acute phase proteins such as C-reactive protein (CRP) may be produced in the liver and secreted into the blood. CRPs physiological role is to bind to phosphocholine expressed on the surface of dead or dying cells (and some types of bacteria) in order to activate the complement system via the C1q complex. Serum amyloid A proteins are another class of acute phase proteins and are a family of apolipoproteins associated with high-density lipoprotein (HDL) in plasma that increase in levels in response to inflammatory stimuli. Cysteine-rich secretory protein 3 (CRISP3) is another acute-phase protein, expressed mainly in mononuclear cells. Its expression is reportedly upregulated in prostate cancer, and is a precursor of recurrence after radical prostatectomy for localized prostate cancer.

Anti-nuclear antibodies (ANA) are autoantibodies directed against the contents of the cell nucleus. They are present in higher than normal numbers in autoimmune disease. The ANA test measures the pattern and amount of autoantibody which can attack the body's tissues as if they were foreign material. Autoantibodies are present in low titers in the general population, but in about 5% of the population their concentration is increased, and about half of this 5% have an autoimmune disease.

Some antigens are found predominantly associated with cancer cells and are termed cancer antigens. CA-125 (cancer antigen 125 or carbohydrate antigen 125; also known as mucin 16 or MUC16) is a member of the mucin family of glycoproteins which may be elevated in the blood of some patients with pancreatic or breast cancer. Carcinoembryonic antigen (CEA) is a type of protein molecule that can be found in many different cells of the body, but is typically associated with certain cancers and the developing fetus. The word "carcinoembryonic" reflects the fact that CEA is produced by some cancers and by the developing fetus.

Typical over-reactions of the host immune response and delayed hypersensitivity reactions are represented by inflammatory infiltrates from T-lymphocytes (CD4+ T helper/inducer cells and CD8+ T cytotoxic/suppressor cells), which are distributed variously between the epithelial and stromal components. Some men with symptoms of chronic prostatitis have evidence of a proliferative CD4/T-cell response to PSA. T-lymphocytes secrete inflammatory mediators such as the complement components C3, C4 and IL-6 in the serum. The concentrations of these markers decrease with the relief of prostatitis symptoms.

The concept of using more than one biomarker to diagnose prostate cancer to improve the accuracy of the PSA test and to increase its prognostic value has been analyzed by a number of investigators. Patterns of biomarker levels in serum have been compared to cancer staging tools as the T (type) classification, N (node) classification, Gleason score and prostate specific antigen (PSA) value before therapy and disease grade. Serum levels of alkaline phosphatase (ALP), lactate dehydrogenase (LDH), chromogranin A (CHGA), serum calcium, and hemoglobin platelet count indicators that add to the accuracy of a PSA value are used by physicians to assess treatment modalities but have not been widely used for prognostic assessment. Large retrospective clinical studies have been undertaken to determine whether disease-specific survival assessed using univariate and multivariate Cox's proportional hazards model analyzes is correlated with patterns of biomarker expression before, during and after treatment.

New prognostic indices clinically applicable for patients with metastatic or late stage (Stage IV) prostate cancer are needed to assess efficacy of treatments because prostate-specific antigen (PSA) tests fail to reflect the prognostic outcome. The PSA/prostatic acid phosphatase (PAP) ratio has been tested as a prognostic index while serum levels of CRP, PSA, CHGA and ALP have been shown to increase and haemoglobin levels have been shown to decrease with advancing extent of disease (EOD) on bone scan EOD grade, and have variously been associated with disease-specific survival. However none of these biomarkers have entered routine diagnostic or prognostic use for prostate cancer.

There thus remains a need in the art for an accurate test for all forms of prostate cancer.

SUMMARY

The present invention provides a minimally invasive test that can be employed to detect prostate cancers, to distinguish prostate cancers from benign prostate hypertrophy (BPH) and prostatitis, and to detect prostate cancers in asymptomatic men whose prostate cancer may produce low levels of PSA, with high sensitivity and specificity. The disclosed methods detect multiple biomarkers and correlate their expression levels with the presence or absence of different prostatic diseases and/or stages of prostate cancer. In certain embodiments, the methods utilize patterns of expression of biomarkers to distinguish between indolent cancers which have a low likelihood of progressing to a lethal disease, and more aggressive forms of prostate cancer which are life threatening and require treatment.

In one aspect, the present disclosure provides methods for diagnosing the presence of prostate cancer in a subject, comprising: (a) detecting the levels of expression of the polypeptide biomarkers prostate specific antigen (PSA), kallikrein-2 (KLK2), C reactive protein (CRP), cysteine-rich secretory protein 3 (CRISP3) and chromogranin A (CHGA) in a biological sample obtained from the subject; and (b) comparing the levels of expression of the polypeptide biomarkers in the biological sample with predetermined threshold values, wherein levels of expression of at least two, at least three or at least four of the plurality of polypeptide biomarkers above the predetermined threshold values are indicative of the presence of prostate cancer in the subject. In certain embodiments, the disclosed methods further comprise detecting the level of expression of at least one additional polypeptide biomarker selected from the group consisting of: prostatic acid phosphatase (PAP, also called ACP3, human acid phosphatase 3, prostatic), lactate hydrogenase (LDH) and bone alkaline phosphatase.

The polypeptide sequences for PSA, KLK-2, CRP, CHGA, PAP, LDH, bone alkaline phosphatase and CRISP3 are provided in SEQ ID NO: 1-14, respectively. In certain embodiments, the methods disclosed herein include detecting the level of expression of a polypeptide comprising a sequence of SEQ ID NO: 1-14, or a variant thereof, as defined herein.

In a related aspect, methods for diagnosing the presence of different types and/or stages of prostate cancer are provided. In one embodiment, methods for diagnosis of early stage prostate cancer in a subject are provided, such methods comprising detecting the expression levels of at least PSA and either CRP or CRISP3, or PSA and both CRP and CRISP3 in a biological sample obtained from the subject, wherein levels of expression of PSA, CRP and/or CRISP3 above predetermined threshold values are indicative of the presence of early stage prostate cancer in the subject. In another embodiment, methods for diagnosing the presence of asymptomatic prostate cancer in a subject are provided, such methods comprising detecting the levels of expression of at least PSA and KLK2 in a sample obtained from the subject, wherein levels of expression of PSA and KLK2 above predetermined threshold values indicate the presence of asymptomatic prostate cancer in the subject. In yet a further embodiment, methods for diagnosing the presence of metastatic prostate cancer in a patient are provided, such methods comprising detecting the levels of expression of PSA, CRP, CRISP3, CHGA and bone alkaline phosphatase in a biological sample obtained the subject, wherein levels of expression of PSA, CRP, CRISP3, CHGA and bone alkaline phosphatase above the predetermined threshold values indicate the presence of metastatic prostate cancer in the subject.

Biological samples that can be effectively employed in the disclosed methods include, but are not limited to, urine, blood, serum, and biopsy tissue.

In certain embodiments, the expression levels of the polypeptide biomarkers employed herein are quantified by immunoassay, such as enzyme-linked immunoassay (ELISA) technology. In specific embodiments, the levels of expression of the polypeptide biomarkers are determined by contacting the biological sample with antibodies, or antigen binding fragments thereof, that selectively bind to the polypeptide biomarkers; and detecting binding of the antibodies, or antigen binding fragments thereof, to the polypeptide biomarkers. The binding agents employed in the disclosed methods and compositions are preferably labeled with a detectable moiety.

For example, the level of a polypeptide biomarker in a sample can be assayed by contacting the biological sample with an antibody, or antigen binding fragment thereof, that selectively binds to the target biomarker (referred to as a capture molecule or antibody), and detecting the binding of the antibody, or antigen-binding fragment thereof, to the polypeptide biomarker. The detection is generally performed using a second antibody to bind to the capture antibody complexed with its target biomarker. A target biomarker can be an entire protein, or a variant or modified form thereof. ELISA kits for the detection of biomarkers as described herein are commercially available and include pre-coated strip plates, biotinylated secondary antibody, standards, controls (where applicable), buffers, streptavidin-horse radish peroxidise (HRP), tetramethyl benzidine (TMB), stop reagents, and detailed instructions for carrying out the tests including performing standards.

The present disclosure also provides methods for the detection of prostate cancer in a subject wherein the levels of expression of the polypeptide biomarkers in a biological sample are determined simultaneously. For example, in one embodiment, methods for diagnosing the presence of prostate cancer in a subject are provided that comprise: (a) contacting a biological sample obtained from the subject with a plurality of binding agents that selectively bind to a plurality of polypeptide biomarkers disclosed herein for a period of time sufficient to form binding agent-polypeptide biomarker complexes; (b) detecting binding of the binding agents to the plurality of polypeptide biomarkers, thereby determining the levels of expression of the polypeptide biomarkers in the biological sample; and (c) comparing the levels of expression of the plurality of polypeptide biomarkers in the biological sample with predetermined threshold values, wherein levels of expression of at least three of the plurality of polypeptide biomarkers above the predetermined threshold values indicates the presence of prostate cancer in the subject. Examples of binding agents that can be effectively employed in such methods include, but are not limited to, antibodies or antigen-binding fragments thereof.

In a further aspect, the present disclosure provides compositions that can be employed in the disclosed methods. In certain embodiments, such compositions a solid substrate and a plurality of binding agents immobilized on the substrate, wherein each of the binding agents is immobilized at a different, indexable, location on the substrate and the binding agents selectively bind to a plurality of polypeptide biomarkers disclosed herein. In one embodiment, the binding agents selectively bind to a plurality of polypeptide biomarkers comprising PSA, KLK2, CRP, CRISP3 and CHGA. In other embodiments, such compositions additionally comprise binding agents that selectively bind to at least one polypeptide biomarker selected from PAP, LDH and bone alkaline phosphatase. Binding agents that can be employed in such compositions include, but are not limited to, antibodies, or antigen-binding fragments thereof.

In a related aspect, methods for diagnosing the presence of prostate cancer in a subject are provided, such methods comprising: (a) contacting a biological sample obtained from the subject with a composition disclosed herein for a period of time sufficient to form binding agent-polypeptide biomarker complexes; (b) detecting binding of the plurality of binding agents to the plurality polypeptide biomarkers, thereby determining the levels of expression of the plurality of polypeptide biomarkers in the biological sample; and (c) comparing the levels of expression of the plurality of polypeptide biomarkers in the biological sample with predetermined threshold values, wherein levels of expression of at least two of the plurality of polypeptide biomarkers above the predetermined threshold values indicates the presence of prostate cancer in the subject.

In yet another aspect, the present disclosure provides compositions comprising a solid substrate and a plurality of polypeptide biomarkers disclosed herein immobilized on the substrate, wherein each of the polypeptide biomarkers is immobilized at a different, indexable, location on the substrate. In certain embodiments, the plurality of polypeptide biomarkers includes PSA, KLK2, CRP, CRISP3 and CHGA. In other embodiments, the plurality of polypeptide biomarkers further includes at least one polypeptide biomarker selected from the group consisting of: PAP, LDH and bone alkaline phosphatase.

In a related aspect, methods for diagnosing the presence of prostate cancer in a subject, comprising: (a) contacting a biological sample obtained from the subject with a composition including a plurality of polypeptide biomarkers disclosed herein for a period of time sufficient to form autoantibody-polypeptide biomarker complexes; (b) detecting the autoantibody-polypeptide biomarker complexes, thereby determining the levels of autoantibodies in the biological sample; and (c) comparing the levels of autoantibodies in the biological sample with predetermined threshold values, wherein levels of autoantibodies against at least two of the plurality of polypeptide biomarkers above the predetermined threshold values indicates the presence of prostate cancer in the subject.

In another aspect, kits for diagnosing the presence or absence of prostate cancer in a subject are provided, such kits comprising binding agents that specifically bind to the polypeptide biomarkers disclosed herein and instructions for their use.

BRIEF DESCRIPTION OF THE DRAWINGS

Figure 2G:
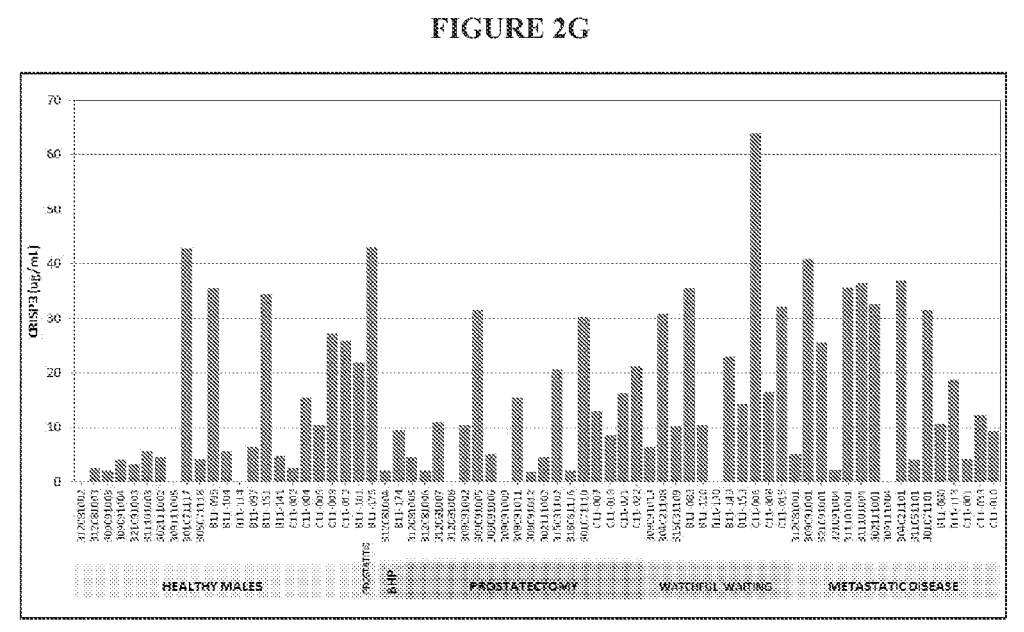

FIGS. 2A-G depict the results of specific ELISAs performed to measure A) KLK2, B) CRP, C) CHGA, D) PAP (ACP3), E) LDH, F) bone alkaline phosphatase, and G) CRISP3 levels in serum of healthy males and males with prostatic diseases. The serum samples measured have been grouped into categories that reflect the status of donors at the time of sample collection: healthy males, asymptomatic males, males with prostatitis, BPH or those who have had prostatectomies, and males on watchful waiting or with metastatic prostate cancer.

DEFINITIONS

Figure 1:
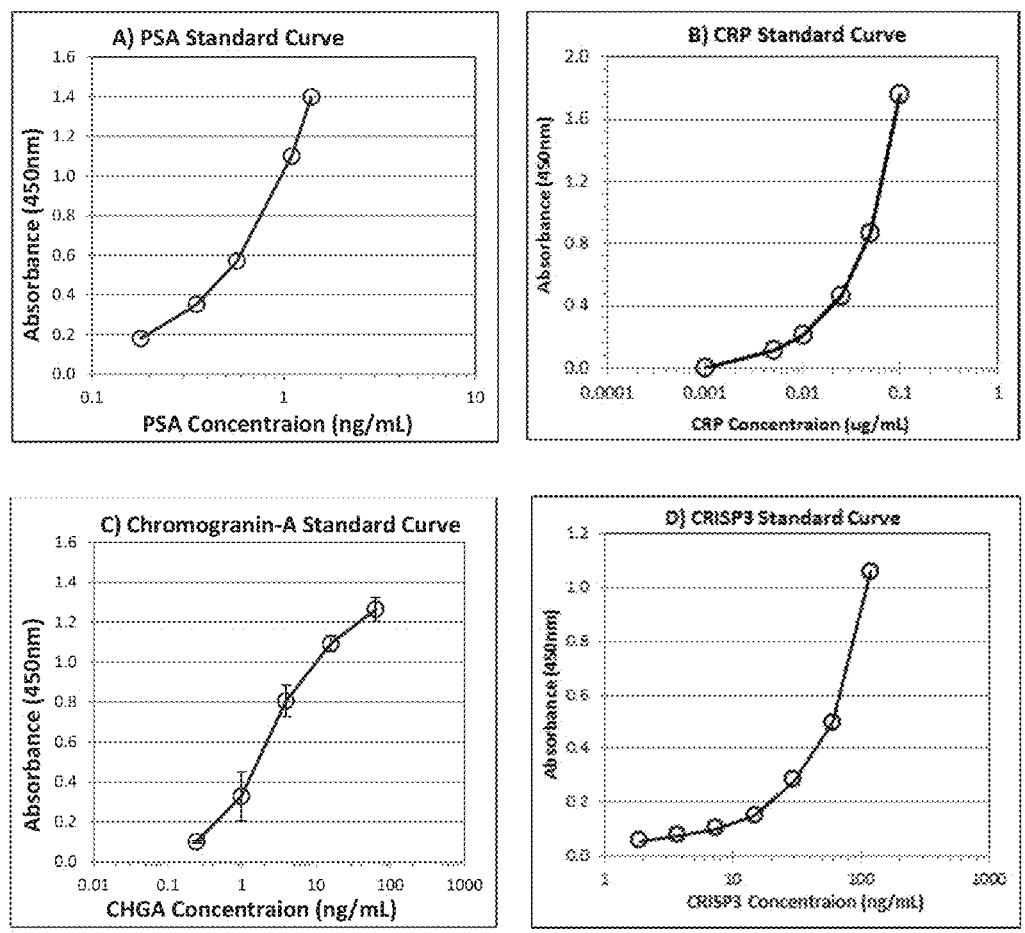
FIGS. 1A-D depict typical standard curves for serum levels of A) PSA, B) CRP, C) CHGA and D) CRISP3 for quantification of enzyme linked immunoassays.
Figure 2A:
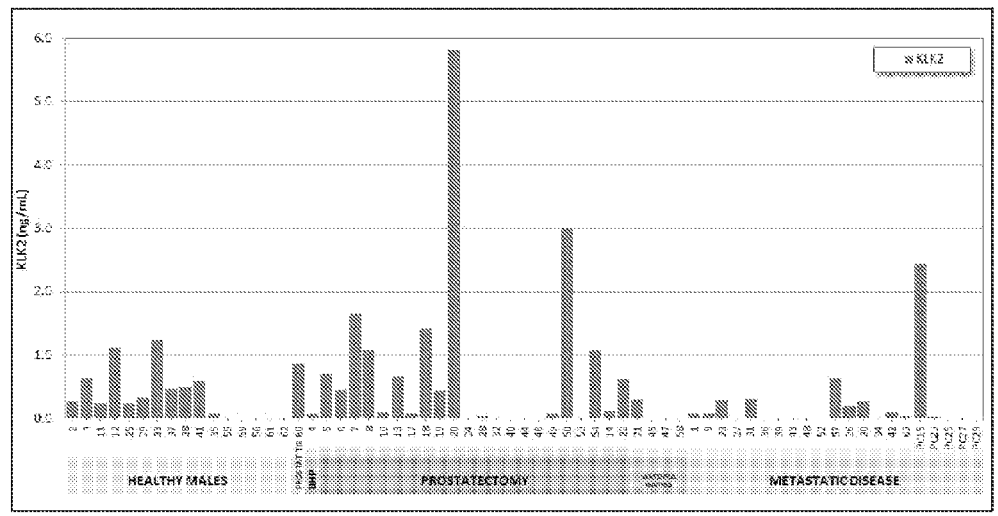
Figure 2B:
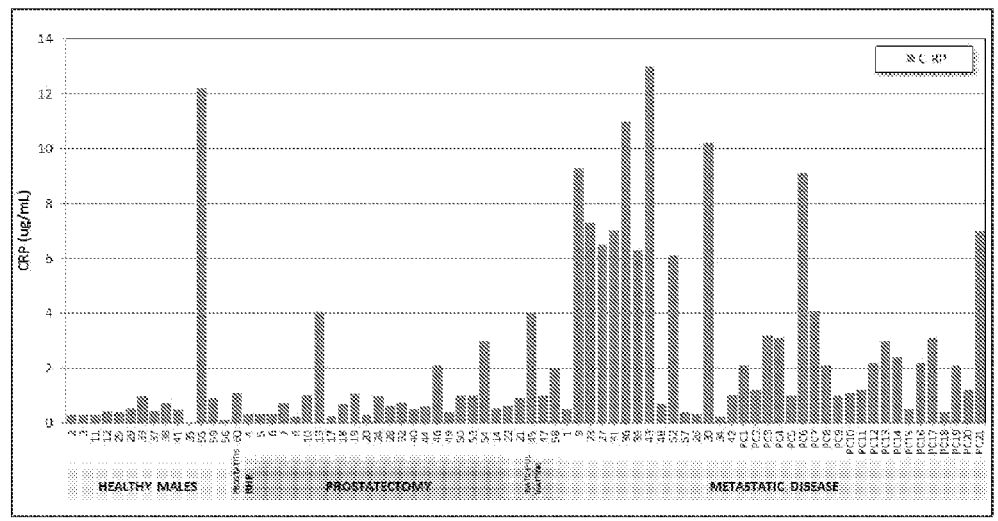
Figure 2C:
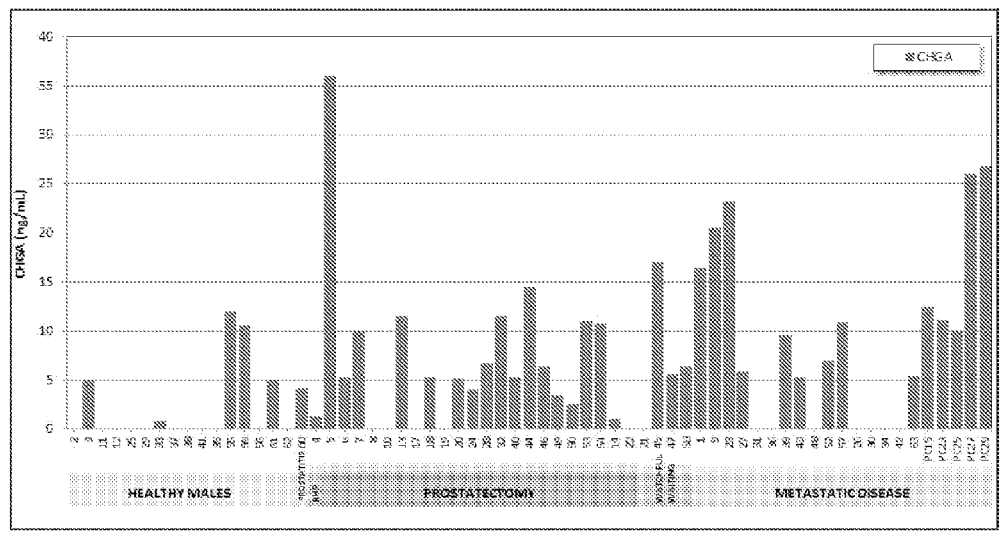
Figure 2D:
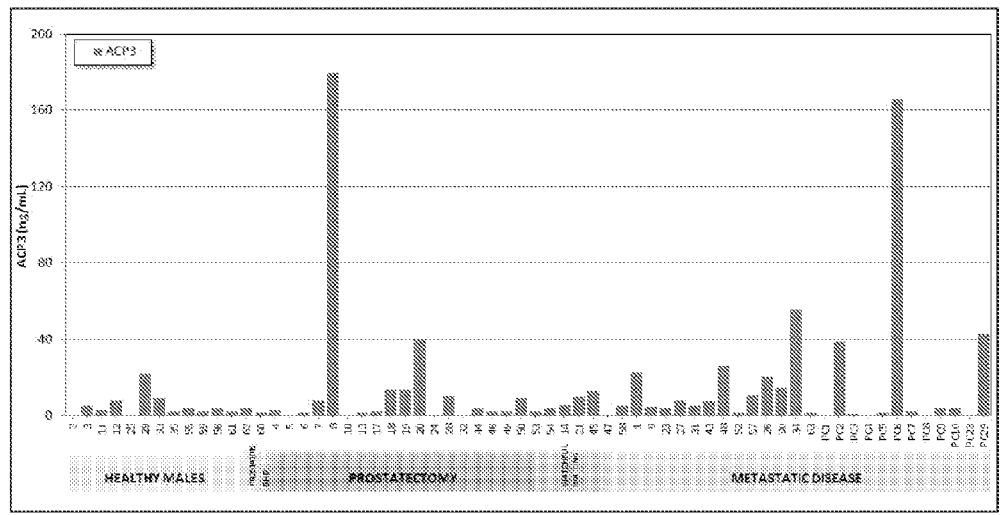
Figure 2E:
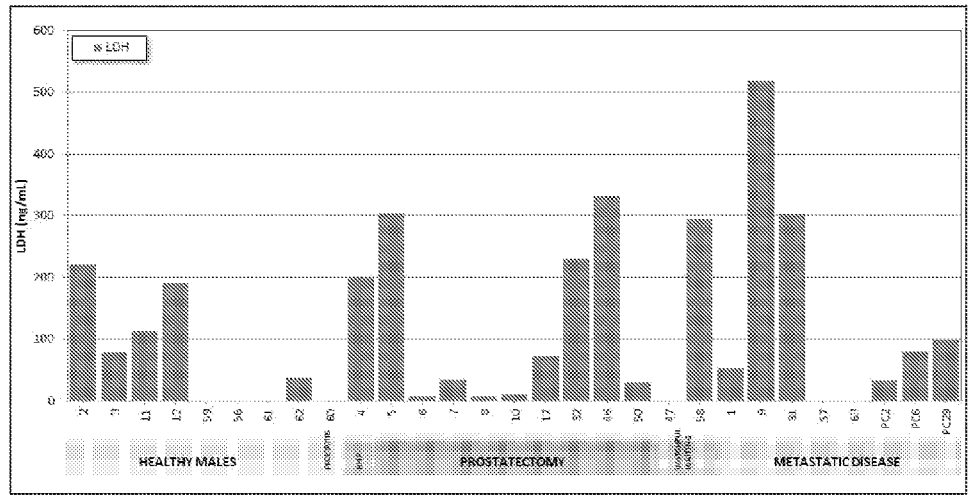
Figure 2F:
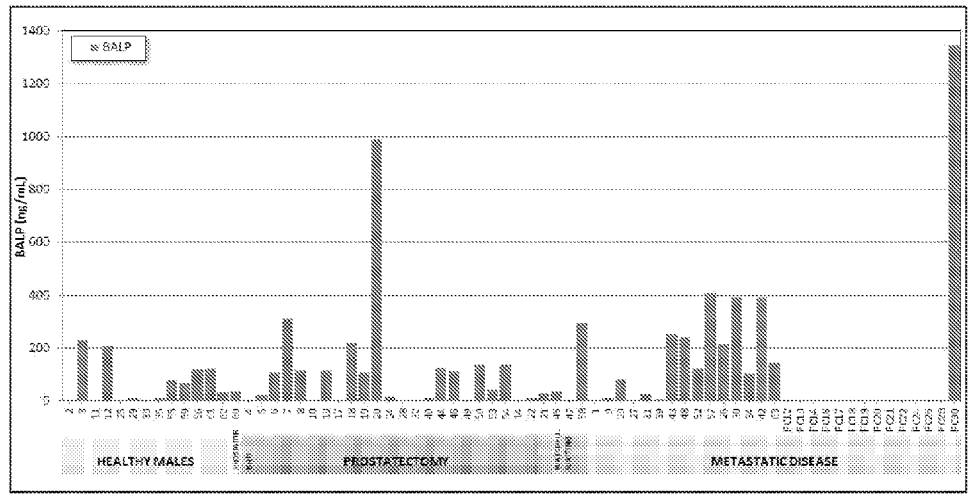

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment; and other body metabolites.

As used herein, the term "antigen" refers to a synthetic peptide, polypeptide, protein or fragment of a polypeptide or protein, or other molecule which elicits an antibody response in a subject, or is recognized and bound by an antibody.

As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a polypeptide biomarker and does not significantly bind to unrelated proteins. Examples of binding agents that can be effectively employed in the disclosed methods include, but are not limited to, proteins and antibodies, such as monoclonal or polyclonal antibodies, or antigen-binding fragments thereof. In certain embodiments, the binding agent binds the polypeptide biomarker with an affinity constant of, for example, greater than or equal to about $1 \times 10^{-6}$ M.

As used herein, the term "subject" refers to a mammal, preferably a human, who may or may not have prostate cancer. Typically, the terms "subject" and "patient" are used interchangeably herein in reference to a human subject.

As used herein, the term "healthy male" refers to a male who has a PSA level in serum of less than 1.0 ng/ml, no evidence of prostate gland abnormality following a DRE and no clinical symptoms of prostatic disorders. Subjects who have no evidence of disease outside the prostate gland but whose PSA is climbing are termed "rising PSA" and subjects who are receiving no further treatments are described as being on "watchful waiting".

As used herein, the term "asymptomatic male" refers to a male who has a PSA level in serum of greater than 8 ng/ml, which is considered indicative of prostate cancer, but whose DRE is inconclusive and who has no symptoms of clinical disease.

The term "benign prostate hypertrophy" (BPH) refers to a prostatic disease with a non-malignant growth of epithelial cells in the prostate gland and the term "prostatitis" refers to another prostatic disease of the prostate, usually due to a microbial infection of the prostate gland. Both BPH and prostatitis can result in increased PSA levels.

As used herein, the term "metastatic prostate cancer" refers to prostate cancer which has spread beyond the prostate gland to a distant site, such as lymph nodes or bone.

As used herein, the term "biopsy tissue" refers to a sample of tissue (e.g., prostate tissue) that is removed from a subject for the purpose of determining if the sample contains cancerous tissue. The biopsy tissue is then examined (e.g., by microscopy) for the presence or absence of cancer.

As used herein, the term "sample" is used herein in its broadest sense to include a sample, specimen or culture obtained from any source. Biological samples include blood products (such as plasma, serum, whole blood and peripheral blood mononuclear cells (PBMCs)), urine, saliva and the like. Biological samples also include tissue samples, such as biopsy tissues or pathological tissues that have previously been fixed (e.g., formalin, snap frozen, cytological processing, etc.).

As used herein, the term "predetermined threshold value of expression" of a biomarker refers to the level of expression of the same biomarker (generally expressed in ng/ml) in a corresponding control/normal sample or group of control/normal samples obtained from normal, or healthy, males, i.e. males who do not have prostate cancer.

As used herein, the term "altered level of expression" of a biomarker in a test biological sample refers to a level that is either below or above the predetermined threshold value of expression for the same biomarker and thus encompasses either high (increased) or low (decreased) expression levels.

As used herein, the term "oligonucleotide specific for a biomarker" refers to an oligonucleotide that specifically hybridizes to a polynucleotide biomarker or a polynucleotide encoding a polypeptide biomarker disclosed herein, and that does not significantly hybridize to unrelated polynucleotides. In certain embodiments, the oligonucleotide hybridizes to the polynucleotide of interest under stringent conditions, such as, but not limited to, prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

As used, herein the term "polynucleotide(s)," refers to a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised.

The term "prognosis" or "providing a prognosis" refers to providing information regarding the likely impact of the presence of prostate cancer (e.g., as determined by the diagnostic methods) on a subject's future health (e.g., the risk of metastasis).

DETAILED DESCRIPTION

As outlined above, the present disclosure provides methods for detecting the presence or absence of prostate cancer in a subject, determining the stage of the prostate cancer and/or the phenotype of the prostate cancer, and/or monitoring treatment of prostate cancer by determining the levels of specific combinations of biomarkers in a biological sample obtained from the subject.

The disclosed methods employ at least five biomarkers selected from those shown in Table 1 below. In one embodiment, the disclosed methods comprise determining the expression levels of PSA, KLK2, CRP, CRISP3 and CHGA in a biological sample taken from a subject, and comparing the expression levels with a predetermined threshold value. In other embodiments, the methods comprise determining the expression levels of PSA, KLK2, CRP, CRISP3 and CHGA, and at least one additional biomarker selected from PAP, bone alkaline phosphatase and LDH. In certain embodiments, the methods comprise determining the expressions levels of each of the seven biomarkers shown in Table 1. These biomarkers were initially identified through analysis of publicly available prostate cancer microarray databases.

TABLE 1

Biomarkers for Diagnosis of Prostate Cancer

| BIOMARKER | COMMENTS | SEQ ID NO: (AMINO ACID) |
|---|---|---|
| Prostate specific antigen (PSA), also known as kallikrein 3 (KLK3) | Provides PSA levels in serum | 1-4 |
| Kallikrein 2 (KLK2) | KLK2 levels in asymptomatic men used for diagnosis. | 5, 6 |
| Chromogranin A (CHGA; also referred to as CGA) | Detects prostate cancer of neuroendocrine origin | 7 |
| C reactive protein (CRP) | Correlates with strong inflammatory response | 8 |
| Prostatic acid phosphatase or acid phosphatase 2 (PAP or ACP3) | Elevated in 20% localized to prostate, 60% untreated cases, 85% bone metastases | 9 |
| Lactate dehydrogenase (LDH) | Metabolic biomarker | 10-12 |
| Bone alkaline phosphatase | Metastatic bone cancer There are 4 genes in the ALP gene family: intestinal, placental, germ cell and non-tissue specific. The tissue non-specific isoenzyme includes the common serum forms of ALP from bone and liver. Liver and bone ALP are isoforms of the tissue non-specific isoenzyme, differing due to post-translational glycation. | 13 |
| Cysteine-rich secretory protein 3 (CRISP3) | Correlates with strong inflammatory response, expression upregulated in prostate cancer | 14 |

The disclosed methods can be employed to diagnose the presence of prostate cancer in subjects with early stage prostate cancer; subjects who have had surgery to remove the prostate (radical prostatectomy); subjects who have had radiation treatment for prostate cancer; subjects who are undergoing, or have completed, androgen ablation therapy; subjects who have become resistant to hormone ablation therapy; and/or subjects who are undergoing, or have had, chemotherapy.

In certain embodiments, the biomarkers disclosed herein are expressed in subjects with prostate cancer at levels that are at least two-fold higher or lower than, or at least two standard deviations above or below, the mean level in normal, healthy individuals, or are at least two-fold higher or lower than, or at least two standard deviations above or below, a predetermined threshold of expression.

In certain embodiments, panels of isolated prostate cancer polypeptide biomarkers are provided that include a plurality of polypeptide sequences (for example at least two, three, four, five, six or seven sequences) selected from SEQ ID NO: 1-14. In related embodiments, panels of binding agents, such as antibodies or antibody fragments, that are specific for the disclosed polypeptide biomarkers are provided, together with panels of oligonucleotides that specifically hybridize to nucleic acid molecules that encode the disclosed polypeptide biomarkers, or that specifically hybridize to the disclosed polynucleotide biomarkers.

All of the biomarkers and binding agents disclosed herein are isolated and purified, as those terms are commonly used in the art. Preferably, the biomarkers and binding agents are at least about 80% pure, more preferably at least about 90% pure, and most preferably at least about 99% pure.

In certain embodiments, the binding agents and/or oligonucleotides employed in the disclosed methods specifically bind to a variant of a polypeptide biomarker or polynucleotide biomarker disclosed herein. As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 80%, 85%, 90%, 95%, 96%, 97%, 98% or 99%) identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100.

In addition to exhibiting the recited level of sequence identity, variants of the disclosed polypeptide biomarkers are preferably themselves expressed in subjects with prostate cancer at levels that are higher or lower than the levels of expression in normal, healthy individuals.

Variant sequences generally differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptide and polynucleotide sequences may be aligned, and percentages of identical amino acids or nucleotides in a specified region may be determined against another polypeptide or polynucleotide sequence, using computer algorithms that are publicly available. The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity.

Two exemplary algorithms for aligning and identifying the identity of polynucleotide sequences are the BLASTN and FASTA algorithms. The alignment and identity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia, Charlottesville, Va. 22906-9025. The FASTA algorithm, set to the default parameters described in the documentation and distributed with the algorithm, may be used in the determination of polynucleotide variants. The readme files for FASTA and FASTX Version 2.0x that are distributed with the algorithms describe the use of the algorithms and describe the default parameters.

The BLASTN software is available on the NCBI anonymous FTP server and is available from the National Center for Biotechnology Information (NCBI), National Library of Medicine, Building 38A, Room 8N805, Bethesda, Md. 20894. The BLASTN algorithm Version 2.0.6 [Sep. 10, 1998] and Version 2.0.11 [Jan. 20, 2000] set to the default parameters described in the documentation and distributed with the algorithm, is preferred for use in the determination of variants according to the present invention. The use of the BLAST family of algorithms, including BLASTN, is described at NCBI's website and in the publication of Altschul, et al., "Gapped BLAST and PSI-BLAST: a new generation of protein database search programs," *Nucleic Acids Res.* 25:3389-3402, 1997.

In an alternative embodiment, variant polypeptides are encoded by polynucleotide sequences that hybridize to a disclosed polynucleotide under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

An "antigen-binding fragment" of an antibody refers to the part of the antibody that participates in antigen binding. The antigen binding site is formed by amino acid residues of the N-terminal variable ("V") regions of the heavy ("H") and light ("L") chains.

Antibodies may be prepared by any of a variety of techniques known to those of ordinary skill in the art (see, for example, Harlow and Lane, *Antibodies: A Laboratory Manual*, Cold Spring Harbor Laboratory, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (*Eur. J. Immunol.* 6:511-519, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells (e.g. bacteria) or eukaryotic cells (e.g. yeast, insect or mammalian cells) and further purified as necessary using well known methods.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., *J. Mol. Biol.* 296:254:57-86, 2000; Krebs et al., *J. Immunol. Methods* 254:67-84, 2001; U.S. Pat. No. 6,300,064).

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent $V_H$::$V_L$ heterodimer including an antigen-binding site which retains much of the antigen recognition and binding capabilities of the native antibody molecule (Inbar et al., *Proc. Natl. Acad. Sci. USA* 69:2659-2662 (1972); Hochman et al., *Biochem.* 15:2706-2710 (1976); and Ehrlich et al., *Biochem.* 19:4091-4096 (1980)).

Antibody fragments that specifically bind to the polypeptide biomarkers disclosed herein can also be isolated from a library of scFvs using known techniques, such as those described in U.S. Pat. No. 5,885,793.

A wide variety of expression systems are available in the art for the production of antibody fragments, including Fab fragments, scFv, $V_L$ and $V_H$s. For example, expression systems of both prokaryotic and eukaryotic origin may be used for the large-scale production of antibody fragments. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins.

Antibodies that bind to the polypeptide biomarkers employed in the present methods, together with ELISA kits that employ such antibodies for the detection of the biomarkers employed herein, are well known to those of skill in the art and are available commercially.

In certain embodiments, the expression level of one or more polypeptide biomarkers disclosed herein is determined using a binding agent, such as a protein, antibody or antibody fragment, that specifically binds to the polypeptide biomarker of interest, for example in an enzyme-linked immunosorbent assay (ELISA), radioimmunoassay, antibody array, Western blot, immunohistochemical, immunoprecipation or immunofluoresence assay. Methods for performing such assays are well known to those of skill in the art.

In one ELISA method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the ELISA is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US 2010/0093557 A1. Methods for the automation of immunoassays are well known in the art and include, for example, those described in U.S. Pat. Nos. 5,885,530, 4,981, 785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture antibody being positioned at a specific, pre-determined, location on the substrate. Methods for performing assays employing such arrays include those described, for example, in US Patent Application Publication nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP®) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

The expression level of one or more polypeptide biomarkers in a biological sample can also be determined by mass spectrometry, in particular liquid chromatography-mass spectrometry (LC-MS) and gas chromatography-mass spectrometry (GC-MS), using methods well known to those of skill in the art.

The expression levels of one or more polynucleotide biomarkers in a biological sample can be determined, for example, using one or more oligonucleotides that are specific for the biomarker. For example, the levels of mRNA corresponding to a prostate cancer biomarker disclosed herein can be detected using oligonucleotides in Southern hybridizations, in situ hybridizations, and quantitative real-time PCR amplification (qRT-PCR). A plurality of oligonucleotides specific for a plurality of biomarkers can be employed in an array format wherein each oligonucleotide is immobilized at a predetermined location on a substrate, such as nitrocellulose membrane. Methods for performing such assays are well known to those of skill in the art.

The oligonucleotides employed in the disclosed methods are generally single-stranded molecules, such as synthetic antisense molecules or cDNA fragments, and are, for example, 6-60 nt, 15-30 or 20-25 nt in length.

Oligonucleotides specific for a polynucleotide that encodes a polypeptide biomarker disclosed herein are prepared using techniques well known to those of skill in the art. For example, oligonucleotides can be designed using known computer algorithms to identify oligonucleotides of a defined length that are unique to the polynucleotide, have a GC content within a range suitable for hybridization, and lack predicted secondary structure that may interfere with hybridization. Oligonucleotides can be synthesized using methods well known to those in the art. For use in array formats, the oligonucleotides may be synthesized directly on the surface of a substrate. Oligonucleotides specific for the prostate cancer biomarkers disclosed herein are known in the art and are commercially available.

In certain embodiments, the oligonucleotides are labeled using one or more detectable moieties. DNA or mRNA isolated from a biological sample is contacted with the labeled oligonucleotides under conditions that allow for formation of hybridization complexes, and the amount of label associated with the hybridization complexes is measured and compared to a standard value.

In one method, the expression level of one or more prostate cancer biomarkers disclosed herein is determined by first collecting urine from a subject following DRE or prostate massage via a bicycle or exocycle. RNA is isolated from the urine sample and amplified using known techniques, such as those described by Laxman et al. (Neoplasia 2006, 8:885-8) and the expression level of mRNA corresponding to the biomarker is determined by, for example, quantitative PCR or RT-PCR using one or more oligonucleotides specific for the biomarker of interest.

For tests involving alterations in RNA expression levels, it is essential to ensure adequate standardization. Accordingly, in tests such as quantitative real time PCR or small scale oligonucleotide microarrays, at least one expression standard selected is employed.

The present disclosure further provides diagnostic panels including a plurality of binding agents (for example, antibodies) or oligonucleotides that are specific for a plurality (for example, two, three, four, five, six or seven) of the prostate cancer biomarkers disclosed herein. In certain embodiments, such panels are in the form of arrays, or microarrays, in which the binding agents or oligonucleotides are immobilized at specific locations on a substrate. The binding agents and oligonucleotides are preferably labeled such that the size and signal intensity of each labeled complex formed between the biomarker and the binding agent/oligonucleotide are individually distinguishable. Alternatively, diagnostic panels are provided in which the biomarkers disclosed herein are immobilized at specific locations on a substrate. The biomarkers are preferably labeled such that the size and signal intensity of labeled complexes formed between the biomarkers and autoantibodies present in a biological sample are individually distinguishable. Kits comprising such diagnostic panels and instructions for their use are also provided. Such kits can also include other components required to carry out the assay, such as buffers, preservatives, wash solutions, etc.

The following examples are intended to illustrate, but not limit, this disclosure.

EXAMPLES

Methods for Examples Relating to Protein Biomarkers

Human ethics approval for the studies described herein was obtained from the Northern X Regional Ethics Committee of New Zealand. A total of 102 blood samples were obtained from subjects who were either volunteer donor healthy males or prostate cancer patients. The distribution of donors with respect to prostate disease status and age is shown in Tables 2A (for PSA, KLK2, CRP, CHGA, PAP (ACP3), LDH and bone alkaline phosphatase assays) and 2B (for CRISP3 assay), below.

TABLE 2A

Characterization of Blood Donors for PSA, KLK2, CRP, CHGA, PAP (ACP3), LDH and bone alkaline phosphatase assays

| Donor status | Number of Donors | Donor Age Range |
| --- | --- | --- |
| Healthy males | 24 | 33-72 |
| Watchful waiting | 8 | 60-70 |
| Prostatitis | 1 | 60 |

TABLE 2A-continued

Characterization of Blood Donors for PSA, KLK2, CRP, CHGA, PAP (ACP3), LDH and bone alkaline phosphatase assays

| Donor status | Number of Donors | Donor Age Range |
| --- | --- | --- |
| Benign Prostatic Hyperplasia | 1 | 63 |
| Asymptomatic males | 3 | 62-69 |
| Prostatectomy performed between 1 and 2 years prior to donating blood sample | 21 | 55-69 |
| Metastatic disease | 44 | 62-78 |

TABLE 2B

Characterization of Blood Donors for CRISP3 assay

| Donor status | Number of Donors | Donor Age Range |
| --- | --- | --- |
| Healthy males | 21 | 31-86 |
| Watchful waiting | 11 | 45-71 |
| Prostatitis | 2 | 60 |
| Benign Prostatic Hyperplasia | 2 | 63-70 |
| Prostatectomy performed between 1 and 2 years prior to donating blood sample | 18 | 57-71 |
| Metastatic disease | 16 | 62-70 |

Blood samples obtained from the subjects described above were screened for levels of protein biomarkers in serum using commercially available ELISA diagnostic kits purchased from Holzel Diagnostika, Germany. Assays were performed in 96 well microtitre plates and each plate included the relevant standards supplied by the manufacturer to determine a standard curve. The linear portion of the standard curve was selected for determining scores using linear-log or log-log plots of the standard curve data. Samples for analyzes were diluted to meet the detection ranges for the ELISAs.

The protein and gene expression biomarkers selected for use in the methods disclosed herein are summarized above in Table 1. Typical standard curves for A) PSA, B) CRP, C) CHGA and D) CRISP3 for quantification of enzyme linked immunoassays are shown in FIG. 1.

Example 1

Measurement of PSA, KLK2, CRP, CRISP3, CHGA, PAP, LDH and Bone Alkaline Phosphatase Levels in Serum The results of specific ELISAs performed to measure A) KLK2, B) CRP, C) CHGA, D) PAP, E) LDH, F) bone alkaline phosphatase, and G) CRISP3 levels in individual donor serum samples are shown in FIGS. 2A-G, respectively. The levels of PSA, KLK2, CRP, CHGA and bone alkaline phosphatase in serum samples from healthy males (n=16; age range 32-72 years), asymptomatic males (n=3; age range 60-70 years) and males on watchful waiting (n=5; age range 62-79 years) were determined and used to calculate the mean and standard errors within each group. Similarly, the level of CRISP3 in serum from healthy males (n=21; age range 31-86 years), healthy females (n=5; age range 44-64 years), males on watchful waiting (n=11; age range 45-73 years), males with prostatitis (n=2; age range 60 years), males with benign prostatic hyperplasia (n=2; age range 62-70 years), males having undergone prostatectomy (n=18; age range 57-71 years) and males with metastatic disease (n=16; age range 62-70 years) was determined and used to calculate the mean and standard error within each group. The results are depicted below in Table 3 and show that the mean PSA, CRP and bone alkaline phosphatase values for the asymptomatic and watchful waiting groups were increased above those of the healthy males group, and that the mean CRISP3 value for the watchful waiting group was above that of the healthy males group (asymptomatic group not tested). In addition, the mean KLK2 values were increased in asymptomatic males compared to healthy males, and the mean CHGA values were increased in males on watchful waiting compared to healthy males.

TABLE 3

| Biomarkers | PSA ng/ml | KLK2 ng/ml | CRP µg/ml | CHGA ng/ml | Bone AP ng/ml | CRISP3 µg/ml |
|---|---|---|---|---|---|---|
| Healthy Males | | | | | | |
| MEAN | 0.67 | 0.358 | 2.43 | 6.68 | 40.16 | 10.85 |
| SE | 0.09 | 0.097 | 0.67 | 0.99 | 10.42 | 2.72 |
| Asymptomatic males | | | | | | |
| MEAN | 5.03 | 3.153 | 31.69 | 6.42 | 107.00 | NT |
| SE | 1.160 | 1.485 | 23.105 | 2.654 | 10.234 | NT |
| Watchful waiting | | | | | | |
| MEAN | 6.61 | 0.310 | 24.87 | 9.65 | 92.80 | 22.12 |
| SE | 4.669 | 0.136 | 11.546 | 2.851 | 60.185 | 5.41 |

*NT = not tested

Figure 3:
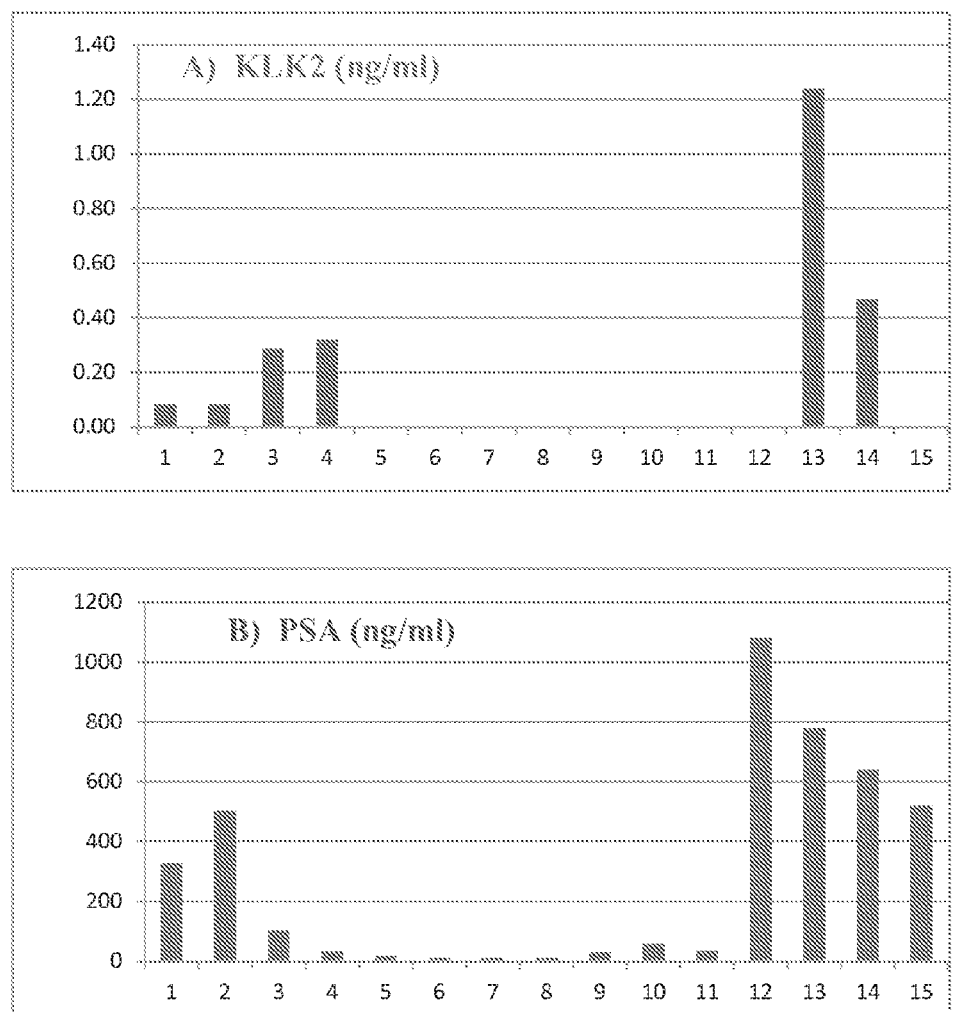
FIGS. 3A and 3B depict the results of ELISA studies in which 15 serum samples from metastatic prostate cancer subjects having high PSA levels were analyzed for KLK2 (FIG. 3A) and PSA (FIG. 3B) in order to determine whether there was any cross reactivity between the capture antibodies used.

As PSA (KLK3) and KLK2 are structurally related and are known to cross react immunologically, these proteins share common epitopes. To ensure that these were not influencing measurements of either PSA or KLK2 in donor serum, 15 donor samples with high PSA values were selected and ELISAs were performed side by side to compare whether KLK2 values increased with the high PSA values, indicating cross reactivity between the capture antibodies for KLK2 and PSA. As shown in FIG. 3, there is no evidence that KLK2 values increase with increasing PSA levels in the samples tested, indicating the capture antibodies used in these studies do not cross react.

Figure 4:
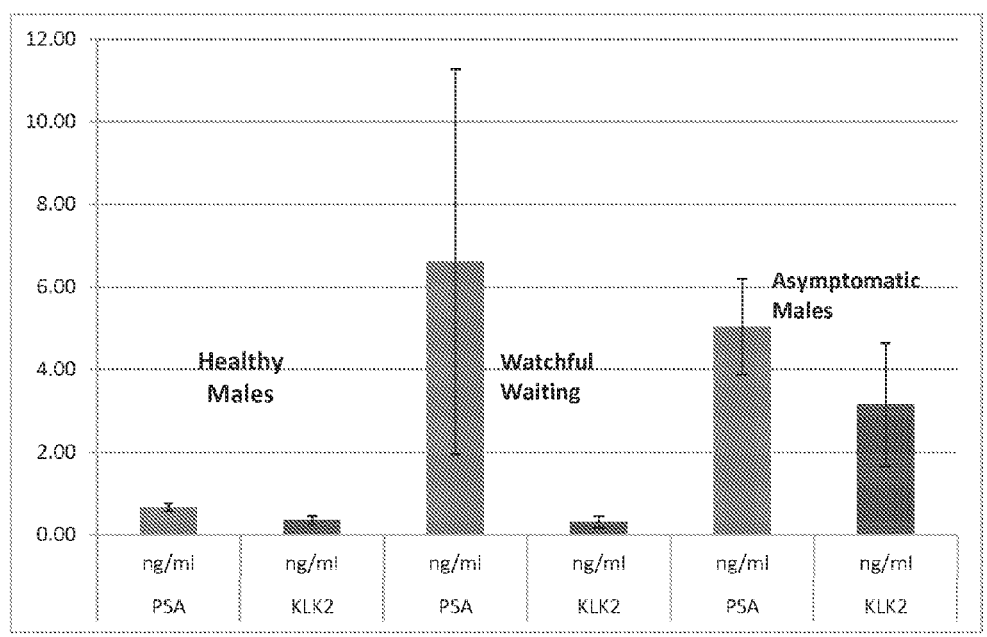
FIG. 4 depicts the PSA and KLK2 levels in serum from healthy males, asymptomatic males and males on watchful waiting as determined by ELISA showing the mean and standard errors.

FIG. 4 depicts a comparison between PSA and KLK2 values in serum samples from healthy males, asymptomatic males and males on watchful waiting. The mean PSA values for samples from healthy males was 0.67, from asymptomatic males was 5.03, and from males on watchful waiting was 6.61. The mean KLK2 values were 0.35 for healthy males, 3.15 for asymptomatic males, and 0.31 for males on watchful waiting. The KLK2 levels for asymptomatic males were thus some 10-fold higher than those on watchful waiting.

Example 2

Inflammatory and Autoimmune Responses in Prostate Cancer Subjects

The term extracted nuclear antigens (ENAs) originally referred to proteins found in a saline extract of mammalian cell nuclei. These proteins are ribonucleoproteins and are commonly used to screen for autoimmune disorders, such as mixed connective tissue disease, Sjögren's syndrome and systemic lupus erythematosus. In order to compare autoimmune responses in prostate cancer subjects to inflammatory responses, antibody levels to ENA and C reactive protein levels in the same serum samples were compared.

Figure 5:
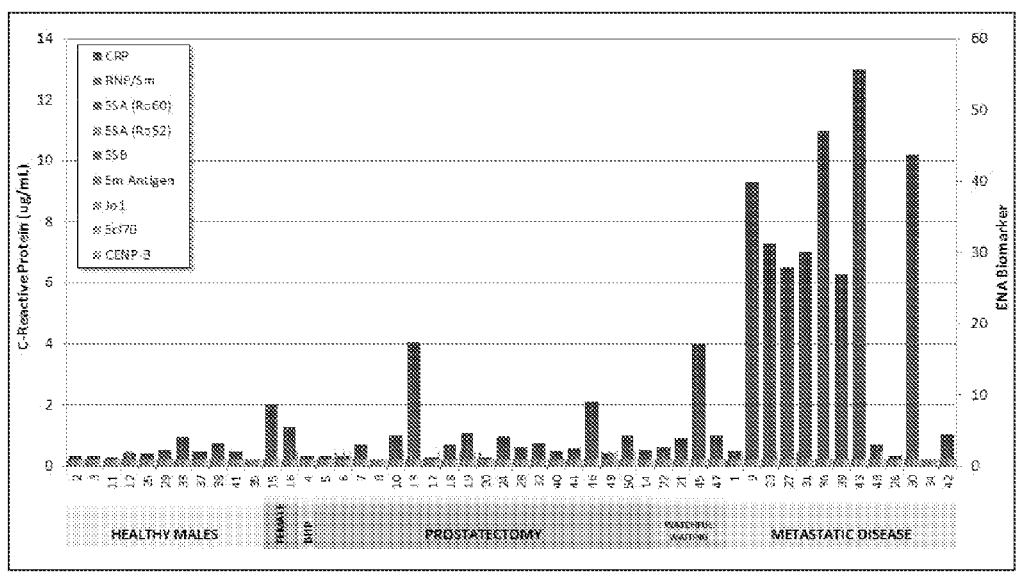
FIG. 5 depicts a comparison of the levels of CRP and antibodies to ENA in serum of healthy males and males with prostatic diseases.

The data depicted in FIG. 5 shows antibody levels to the ENA proteins RNP/Sm, SSA (Ro60), SSA (Ro52), SSB Sm Antigen, Jo1 Scl70, Jo1 Scl70 and CENP-B in serum from healthy donors and from subjects with prostate cancer. These levels, at a serum dilution of 1:2, rarely exceeded a level of two times above background. By contrast, the data indicates that levels of C reactive protein, an acute phase protein, were significantly increased in serum of many patients with prostate cancer, particularly those with metastatic disease. Collectively, these data indicate that the immune responsiveness in prostate cancer subjects is more akin to an inflammatory, or Th1, response than to an autoimmune, or Th2, response.

Example 3

Expression Levels of PSA, KLK2, CRP, CRISP3, CHGA, PAP, LDH and Bone Alkaline Phosphatase in Serum from Healthy Subjects, Prostatectomy Subjects and Metastatic Subjects Donor serum samples were obtained from subjects who had a prostatectomy more than one year prior to donating the sample (n=21; 55-69 years) and subjects who presented with metastatic prostate cancer (n=42; 62-78 years).

Figure 6:
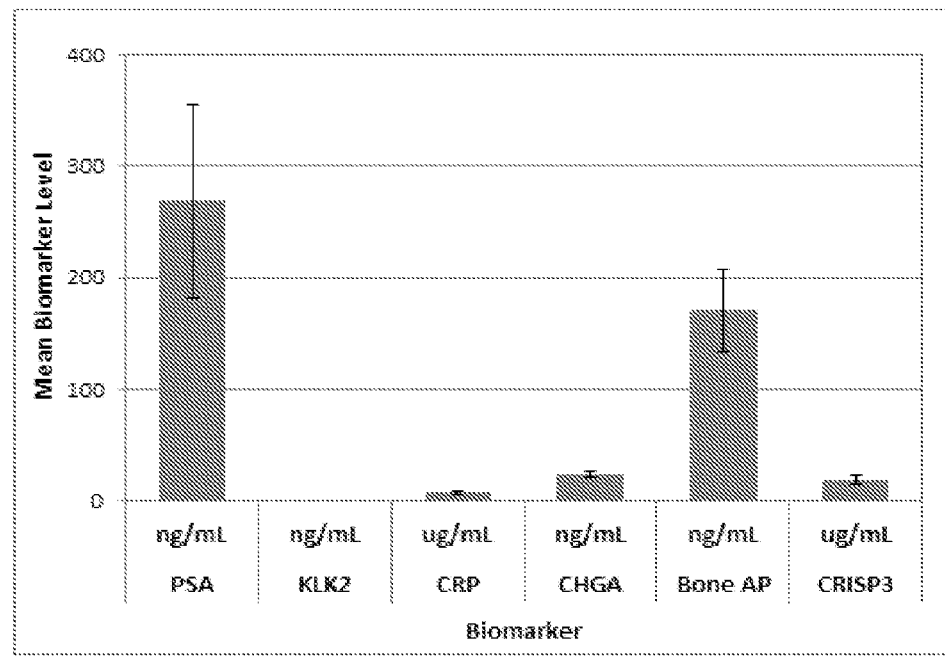
FIG. 6 depicts the levels of PSA, KLK2, CRP, CHGA, bone alkaline phosphatase and CRISP3 in Group A males with metastatic prostate cancer (men who had been diagnosed with disease and who were entering their first treatment with chemotherapy).
Figure 7:
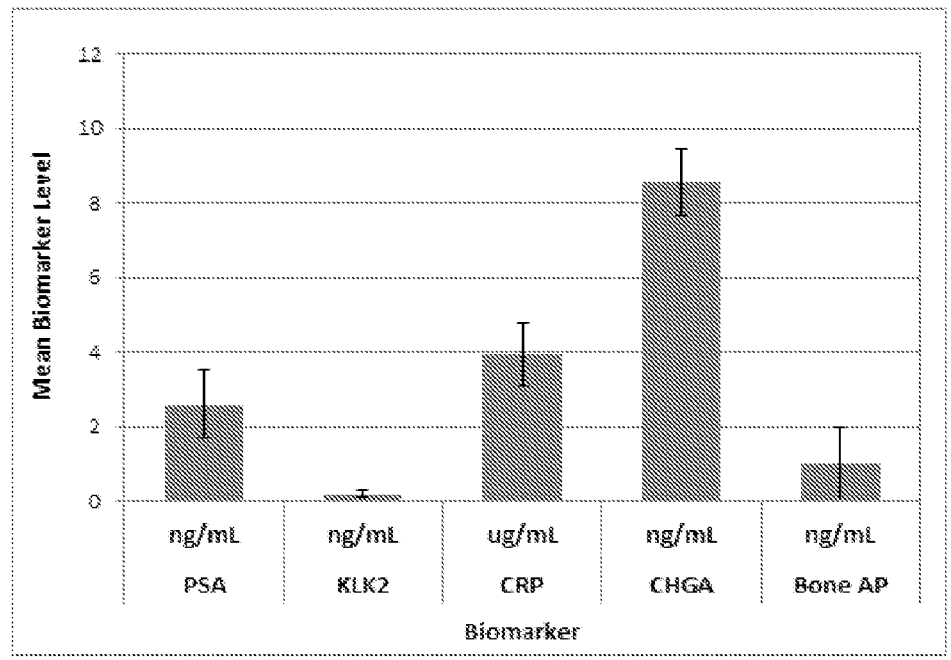
FIG. 7 depicts the levels of PSA, KLK2, CRP, CHGA and bone alkaline phosphatase in Group B males with metastatic prostate cancer (subjects who had been diagnosed with disease and had completed chemotherapy, and in whom the disease had stabilized).

The metastatic prostate cancer subjects fell into two groups, referred to herein as "Metastatic Group A" and "Metastatic Group B". Group A (n=12; 42-73 years) were males who had undergone hormone deprivation therapy, were considered hormone resistant and were commencing, or had commenced, chemotherapy within one year of providing a sample for this study. Chemotherapy included different regimes for each patient with some having ketoconazole, Leukine® or taxotere treatment (FIG. 6). Group B (n=30; 62-78 years) were males who had undergone more extensive treatment (FIG. 7). A summary of the age and treatment status of Group B subjects is shown in Table 4.

TABLE 4

| Summary of Metastatic Group B Subjects | |
|---|---|
| Number of blood samples | 30 |
| Age range | 49-78 |
| Ethnicity | Caucasian, African American |
| Range of treatments | Androgen deprivation therapy, radiation, Zometa, Tricor, Lipitor, Simvastatin, Omeprazole, Furosemide, Dexamethasone, Klor-Con M20, Vitamin D, Benadryl, Decadron, Pepcid, Carboplatin, Taxol |

The levels of PSA, KLK2, CRP, CRISP3, CHGA, PAP, LAH and bone alkaline phosphatase (BAP) in serum from the subjects, as determined by ELISA, are shown in Table 5 below. As can be seen from the data, distinct patterns of increased CRP, CHGA and bone alkaline phosphatase (BAP) levels were observed in serum from patients with metastatic prostate cancer.

TABLE 5

| Biomarkers | PSA ng/ml | KLK2 ng/ml | CRP μg/ml | CHGA ng/ml | BAP ng/ml | PAP ng/ml | LDH ng/ml | CRISP3 μg/ml |
|---|---|---|---|---|---|---|---|---|
| Healthy Males | | | | | | | | |
| MEAN | 0.67 | 0.35 | 2.43 | 6.68 | 40.16 | 4.78 | 80.1 | 10.85 |
| SE | 0.09 | 0.09 | 0.67 | 0.99 | 10.42 | 1.32 | 28.31 | 2.72 |
| Prostatectomy | | | | | | | | |
| MEAN | 0.54 | 0.484 | 9.10 | 9.38 | 110.73 | 15.5 | 113.8 | 13.97 |
| SE | 0.09 | 0.13 | 3.23 | 2.00 | 20.51 | 9.32 | 44.92 | 3.97 |
| Metastatic Cancer Group A | | | | | | | | |
| MEAN | 268.73 | 0.126 | 73.36 | 23.93 | 171.09 | 11.90 | 174.80 | 19.14 |
| SE | 86.86 | 0.044 | 16.61 | 2.29 | 36.86 | 4.13 | 102.50 | 3.69 |
| Metastatic Cancer Group B | | | | | | | | |
| MEAN | 2.61 | 0.189 | 39.53 | 8.56 | 1.00 | 47.96 | 73.3 | NT |
| SE | 0.934 | 0.097 | 8.52 | 0.88 | 1 | 12.81 | 19.37 | NT |

*NT = not tested

Methods for Examples Relating to Gene Expression Biomarkers

Gene expression analyses were performed using PBMCs from a group of 15 prostate cancer patients and five healthy subjects (three males and two females). The healthy males were determined to be free of prostate cancer and showed no evidence of prostate cancer in a 12 month follow up. Blood was collected at different times over a four month period. The collection times of specific donor samples are shown in Tables 6A and 1B, below, together with an internal code, gender and disease status (CaP=prostate cancer; Norm=healthy subject).

TABLE 6A

Healthy Male Donors

| DONOR | AGE | DATE PBMC COLLECTED | PSA AT PBMC COLLECTION | PSA STATUS | PROSTATE CANCER STATUS; FAMILY HISTORY |
|---|---|---|---|---|---|
| #2 | 33 | March 2011 | 0.33 | Static | Negative by DRE; Father Gleason 9 |
| #3 | 46 | July 2011 | 0.7 | Static | Negative by DRE; None Known |
| #4 | 60 | June 2011 | 6.5 | Fluctuating up to 6.5 | Negative by DRE; Father (now deceased) high Gleason |
| #7 | 51 | June 2011 | 2.8 | Fluctuating up to 4.0 | Negative by DRE; Brother CaP Gleason 6 |
| #13 | 59 | May 2011 | <0.1 | Stable | Gleason 8, Radiation/Zoladex Treatment Terminated |

TABLE 6B

Prostate Cancer Donors

| DONOR | AGE | DATE PBMC COLLECTED | PSA AT PBMC COLLECTION | PSA STATUS | PROSTATE CANCER STATUS |
|---|---|---|---|---|---|
| #1 | 78 | April 2011 | 6.9 | Rising | Gleason 8; Prostatectomy 24 hrs after PBMC Collection |
| #5 | 73 | July 2011 | 3.8 | Fluctuating up to 5 | PSA Monitoring for suspected CaP |
| #6 | 62 | March 2011 | 0.1 | Rising | Gleason 9/RP/Seminal Vesicle Invasion/ Radiation/Zoladex, last treatment 16 months prior. |
| #8 | 67 | 7 Dec. 2010 & 4 Feb. 2011 | 9 (December 2010) | Falling | Gleason 9, Radiation/ currently on Ketoconazole and Leukine |
| #9 | 62 | 21 Sep. 2010 & 7 Dec. 2010 | 860 (December 2010) | Static | Gleason 9, Radiation/ currently on Ketoconazole and Leukine |

PBMCs were purified by centrifugation over a layer of Ficoll™ Hypaque and RNA extractions using recovered cells were all performed with TRIZOL™ (Invitrogen, Cat#15596-026), according to the manufacturer's instructions. cDNA amplifications were performed with Superscript VILO cDNA Synthesis Kit (Invitrogen, Cat#11754-250) containing (10×) Superscript Enzyme Mix and (5×) VILO Reaction Mix. Briefly, 10 µl of the sample (10 ng/µl final concentration) was added to a PCR tube strip. The master mix was prepared according to the manufacturer's protocol and 10 µl of the master mix was added, mixed by vortexing for a few seconds and centrifuged at 1,000 rpm for a few seconds. Amplification involved the following steps: 10 minutes at 25° C.; 60 minutes at 42° C.; 5 minutes at 85° C.; held at 4° C. Storage of the cDNA was at −20° C.

Quantitative Real Time PCR amplification employed InVitrogen Platinum® SYBR® Green qPCR SuperMix-UDG with ROX (Cat. no. 11744-500). Briefly, cDNA samples retrieved from −20° C. were tested in triplicate. Samples were briefly centrifuged, diluted 1:5 with RNase free water, mixed and centrifuged. 2 µl of each cDNA was transferred to appropriate wells of a 384-well microtitre plate. For a single reaction, 5 µl of Syber green master mix plus 0.2 µl of 10 µM forward and reverse specific primers plus were mixed with 2.6 µl of RNase free water. Then 8 µl of each master mix was transferred to appropriate assays in microwells and the plates sealed with optical plastic. After mixing by vortexing, the plates were centrifuged briefly, and then analysed via qRT-PCR (7900 HT Fast Real Time PCR System, Applied Biosystems).

Conditions used for qRT-PCR are described in Table 7, below.

TABLE 7

Conditions used for qRT-PCR

| Programme | Cycles n. | Dissociation step | Cycles n. |
|---|---|---|---|
| 50° C. × 2 min. | 1 | 95° C. × 15 sec. | |
| 95° C. × 2 min. | 1 | 60° C. × 15 sec. | 1 |
| 95° C. × 15 sec. | 40 | 95° C. × 15 sec. | |
| 60° C. × 1 min. | | | |

Example 4

Figure 8:
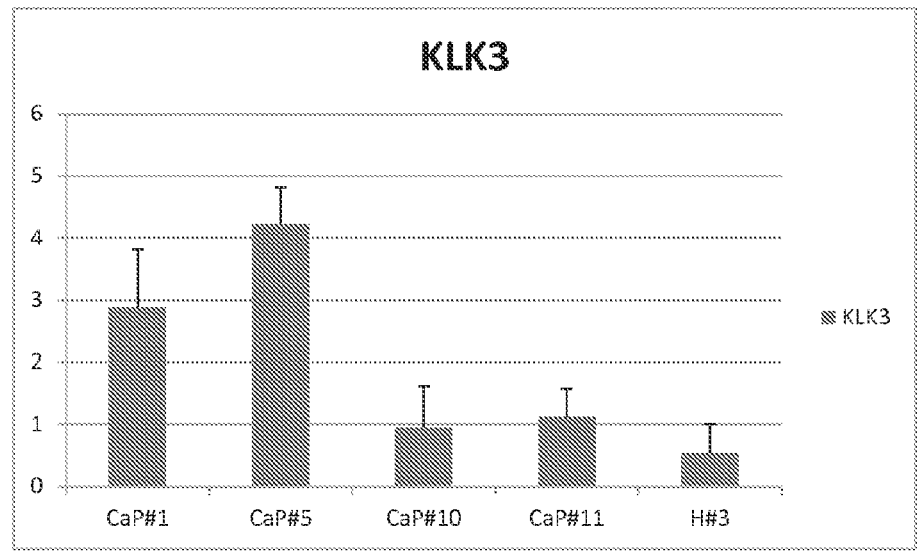
FIG. 8 shows mRNA expression of KLK3 in PBMCs from blood collected from prostate cancer (CaP) and healthy (Normal) donors.

Elevated mRNA Expression of KLK3 in Blood from Prostate Cancer Patients mRNA expression of KLK3 was examined in PBMCs from blood collected from prostate cancer (CaP) and healthy (Normal) donors. The results (shown below in Table 8 and in FIG. 8) showed a significant increase of the specific mRNA level in one or more CaP donor compared to other CaP donors and all healthy donors. All the data was normalized on C19ORF50 and compared with the negative control value of donor #4.

TABLE 8

Elevated KLK3 mRNA expression in prostate cancer donors relative to healthy donor #4
KLK3 normalised on #4

| Code | $2^{-ddCt}$ | Error bars |
|---|---|---|
| CaP #1 | 2.889211 | 0.930156 |
| CaP #5 | 4.22399 | 0.58811 |
| CaP #10 | 0.95007 | 0.663213 |
| CaP #11 | 1.125121 | 0.447677 |
| H #3 | 0.535708 | 0.464292 |

Example 5

Figure 9:
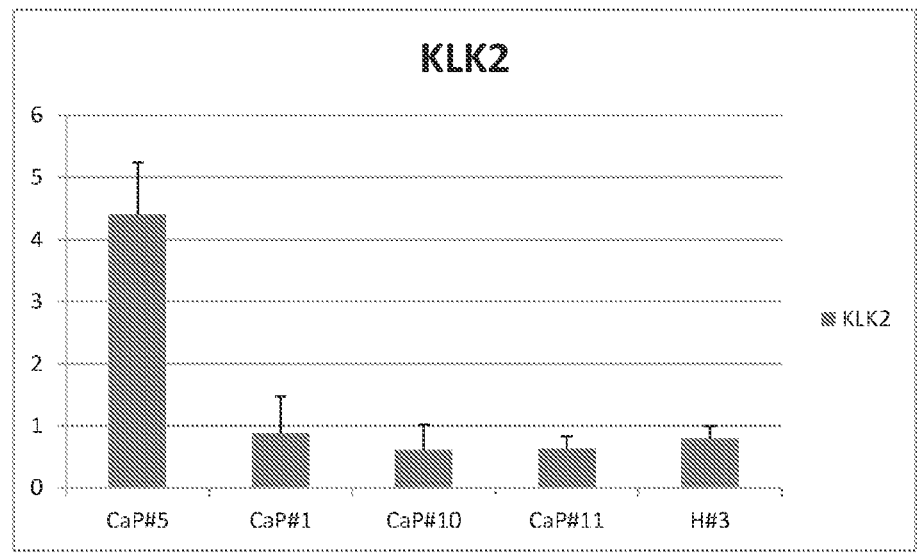
FIG. 9 shows mRNA expression of KLK2 in PBMCs from blood collected from prostate cancer (CaP) and healthy (Normal) donors.

Elevated mRNA Expression of KLK2 in Blood from Prostate Cancer Patients mRNA expression of KLK2 was examined in PBMCs from blood collected from prostate cancer (CaP) and healthy (Normal) donors. The results (shown below in Table 9, and in FIG. 9) showed a significant increase of the specific mRNA level in CaP donor #5 compared to other CaP donors and healthy donors. All the data was normalized on C19ORF50 and compared with the negative control value of donor #3.

TABLE 9

Elevated KLK2 mRNA expression in prostate cancer donors relative to healthy donor #3
KLK2 normalised on #3

| Code | $2^{-ddCt}$ | Error bars |
|---|---|---|
| CaP #5 | 4.40 | 0.84 |
| CaP #1 | 0.88 | 0.59 |
| CaP #10 | 0.60 | 0.42 |
| CaP #11 | 0.64 | 0.20 |
| H #3 | 0.81 | 0.19 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

SEQ ID NO: 1-14 are set out in the attached Sequence Listing. The codes for nucleotide sequences used in the attached Sequence Listing, including the symbol "n," conform to WIPO Standard ST.25 (1998), Appendix 2, Table 1.

The invention claimed is:

1. A method for diagnosing the presence of prostate cancer in a subject, comprising:
   (a) contacting a biological sample obtained from the subject with a composition for a period of time sufficient to form binding agent-polypeptide biomarker complexes, wherein the composition comprises a solid substrate and a plurality of binding agents immobilized on the substrate, wherein each of the binding agents is immobilized at a different, predetermined, location on the substrate and the binding agents specifically bind to a plurality of polypeptide biomarkers, the plurality of polypeptide biomarkers comprising:
      i) at least one sequence selected from SEQ ID NO: 1-4;
      ii) SEQ ID NO: 7;
      iii) SEQ ID NO: 8;
      iv) SEQ ID NO: 13; and
      v) SEQ ID NO: 14;
   (b) detecting binding of the plurality of binding agents to the plurality polypeptide biomarkers, thereby determining the levels of expression of the plurality of polypeptide biomarkers in the biological sample; and
   (c) comparing the levels or expression of the plurality of polypeptide biomarkers in the biological sample with predetermined threshold values,
   wherein levels of expression of the plurality of polypeptide biomarkers comprising;
      i) at least one sequence selected from SEQ ID NO: 1-4;
      ii) SEQ ID NO: 7;
      iii) SEQ ID NO: 8;
      iv) SEQ ID NO: 13; and
      v) SEQ ID NO: 14
   above the predetermined threshold values indicates the presence of prostate cancer in the subject.

2. The method of claim 1, wherein the biological sample is selected from the group consisting of: urine, blood, serum, and biopsy tissue.

3. The method of claim 1, wherein the binding agents are antibodies or antigen-binding fragments thereof.

4. The method of claim 1, wherein the binding agents are labeled with a detectable moiety.

5. The method of claim 4, wherein the detectable moiety is selected from the group consisting of: cheminescent and luminescent agents; radioisotopes, colorimetric agents; and enzyme-substrate labels.

* * * * *